United States Patent
Lewis

(10) Patent No.: US 11,940,626 B1
(45) Date of Patent: *Mar. 26, 2024

(54) DIGITAL EYEWARE PROCEDURES RELATED TO DRY EYES

(71) Applicant: Percept Technologies, Los Altos, CA (US)

(72) Inventor: Scott W. Lewis, Las Vegas, NV (US)

(73) Assignee: Percept, Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/507,744

(22) Filed: Oct. 21, 2021

Related U.S. Application Data

(63) Continuation of application No. 16/138,951, filed on Sep. 21, 2018, now Pat. No. 11,181,740, which is a
(Continued)

(51) Int. Cl.
*G02B 27/01* (2006.01)
*A61B 3/113* (2006.01)
(Continued)

(52) U.S. Cl.
CPC .......... *G02B 27/0172* (2013.01); *A61B 3/113* (2013.01); *G02B 27/0093* (2013.01);
(Continued)

(58) Field of Classification Search
CPC ............ G02B 27/0172; G02B 27/0093; G02B 27/017; G02B 5/30; G02B 2027/0127;
(Continued)

(56) References Cited

U.S. PATENT DOCUMENTS 11,181,740 B1 * 11/2021 Lewis ................ G02B 27/0172
2013/0172829 A1 * 7/2013 Badawi ................ A61F 9/0008
604/294
(Continued)

*Primary Examiner* — Mohammed A Hasan
(74) *Attorney, Agent, or Firm* — Los Altos Law

(57) ABSTRACT

Devices/techniques coupleable to patient sensors, ambient environment, and external sensory input. Devices/techniques receive/maintain information; correlate received/maintained information with measures associated with detecting/monitoring, predict, prevent/treat, and train/reward patient self-care, for dry eyes. Devices/techniques detect/monitor, predict, and prevent/treat dry eyes in real time; and train/reward patients to conduct self-care for dry eyes. The devices/techniques provide adjusted sensory inputs to prevent/treat dry eyes, or to train/reward patients to conduct self-care for dry eyes. The devices/techniques cooperate with other devices, including devices worn by nearby patients, to receive/maintain information about the ambient environment, or communicate with medical personnel. The devices/techniques adjust parameters they use, in response to received information that differs from predictions, to provide superior behavior, and communicate with other devices and medical personnel. Devices/techniques are combined with devices/techniques that perform similar functions for other conditions, migraines/photophobia, neuro-opthalmic disorders, and other ocular conditions, and for combinations of dry eyes with other conditions.

20 Claims, 8 Drawing Sheets

Related U.S. Application Data continuation-in-part of application No. 15/942,591, filed on Apr. 2, 2018, now abandoned, which is a continuation-in-part of application No. 15/460,197, filed on Mar. 15, 2017, which is a continuation-in-part of application No. 14/589,817, filed on Jan. 5, 2015, now Pat. No. 9,658,473, which is a continuation of application No. 14/288,189, filed on May 27, 2014, now abandoned, which is a continuation of application No. 13/965,050, filed on Aug. 12, 2013, now Pat. No. 8,733,927, which is a continuation of application No. 13/841,141, filed on Mar. 15, 2013, now Pat. No. 8,696,113.

(51) Int. Cl.

| | | |
|---|---|---|
| *G02B 27/00* | (2006.01) | |
| *G02C 7/00* | (2006.01) | |
| *G02C 7/10* | (2006.01) | |
| *G02C 7/12* | (2006.01) | |
| *G02C 11/00* | (2006.01) | |
| *G06F 3/01* | (2006.01) | |
| *G02B 5/30* | (2006.01) | |

(52) U.S. Cl.
CPC .............. *G02B 27/017* (2013.01); *G02C 7/00* (2013.01); *G02C 7/101* (2013.01); *G02C 7/12* (2013.01); *G02C 11/10* (2013.01); *G06F 3/011* (2013.01); *G06F 3/013* (2013.01); *G02B 5/30* (2013.01); *G02B 2027/0127* (2013.01); *G02B 2027/0138* (2013.01); *G02B 2027/0141* (2013.01); *G02B 2027/0178* (2013.01); *G02B 2027/0187* (2013.01)

(58) Field of Classification Search
CPC .... G02B 2027/0138; G02B 2027/0141; G02B 2027/0178; G02B 2027/0187; A61B 3/113; G02C 7/00; G02C 7/101; G02C 7/12; G02C 11/10; G06F 3/011; G06F 3/013
USPC ........................................................ 359/588
See application file for complete search history.

(56) References Cited

U.S. PATENT DOCUMENTS

2015/0116465 A1\* 4/2015 Wang .................... H04N 13/30
                                                                    348/51
2015/0161783 A1\* 6/2015 Chang ................... G06T 7/0016
                                                                   382/116

\* cited by examiner

Lenses 120

Patient Eye Features 300

Method 400

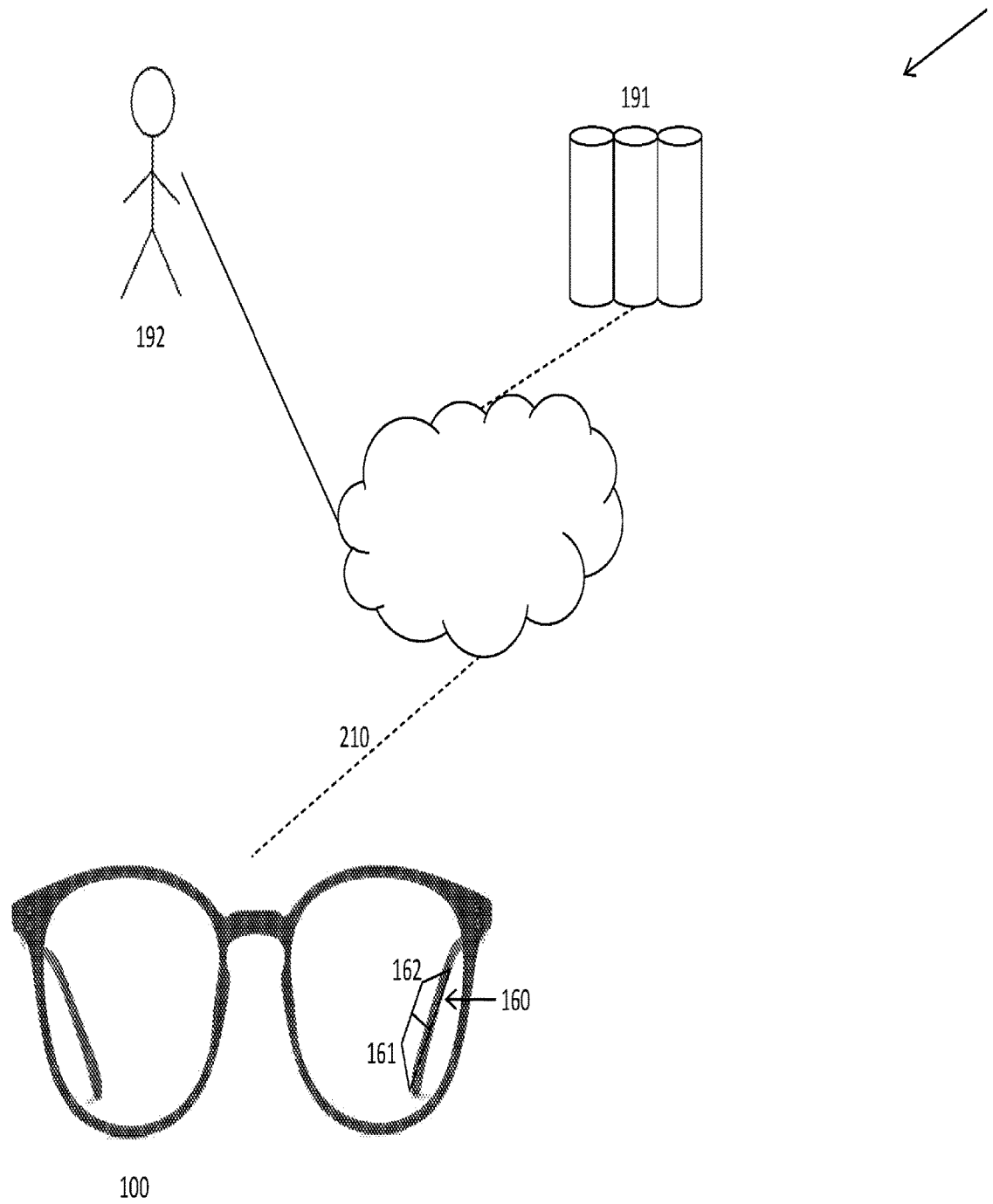

System 600

Method 650

Eye Mask 710

DIGITAL EYEWARE PROCEDURES RELATED TO DRY EYES

INCORPORATED DISCLOSURES

This Application describes technologies that can be used with inventions, and other technologies, described in one or more of the following documents. This Application claims priority, to the fullest extent permitted by law, of these documents.

This Application is a continuation-in-part of
application Ser. No. 15/942,951, filed Apr. 2, 2018, naming inventor Scott LEWIS, titled "Digital Eyewear System and Method for the Treatment and Prevention of Migraines and Photophobia", currently pending;
which is a continuation-in-part of
application Ser. No. 15/460,197, filed Mar. 15, 2017, naming inventor Scott LEWIS, titled "Digital Eyewear Augmenting Wearer's Interaction with their Environment", unpublished, currently pending;
which is a continuation-in-part of
application Ser. No. 14/589,817, filed Jan. 5, 2015, naming inventor Scott LEWIS, titled "Enhanced Optical and Perceptual Digital Eye-wear", now U.S. Pat. No. 9,658,473;
which is a continuation of
application Ser. No. 14/288,189, filed May 27, 2014, naming inventor Scott LEWIS, titled "Enhanced Optical and Perceptual Digital Eyewear", now abandoned;
which is a continuation of
application Ser. No. 13/965,050, filed Aug. 12, 2013, naming inventor Scott LEWIS, titled "Enhanced Optical and Perceptual Digital Eyewear", now U.S. Pat. No. 8,733,927;
which is a continuation of
application Ser. No. 13/841,141, filed Mar. 15, 2013, naming inventor Scott LEWIS, titled "Enhanced Optical and Perceptual Digital Eyewear", now U.S. Pat. No. 8,696,113.

Each of these documents is hereby incorporated by reference as if fully set forth herein. Techniques described in this Application can be elaborated with detail found therein. These documents are sometimes referred to herein as the "Incorporated Disclosures," the "Incorporated Documents," or variants thereof.

COPYRIGHT NOTICE

A portion of the disclosure of this patent document contains material subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND

Field of the Disclosure

This Application generally describes techniques relating to digital eyewear procedures related to dry eyes, digital eyewear disposed for use with techniques relating to dry eyes, and other issues.

Related Art

"Dry eyes" is a medical condition in which the quantity or quality of tears fails to keep the surface of the eye adequately lubricated (National Institutes of Health, "Facts About Dry Eye"). This can result from a decrease in normal lubrication of the eyes, tissues, or membranes relating to the eyes. "Dry eyes" is sometimes referred to as "dry eye syndrome," or keratoconjunctivitis sicca ("dryness of the cornea and conjunctiva"). Dry eyes can result when the eye does not produce enough tears, when tears evaporate too rapidly, or when irritants or other factors interfere with natural lubrication of the eye. For example, infections and exposure to smoke can cause dryness of the eyes. Some known causes of dry eyes include: excess use of contact lenses, blockage or infection of the tear ducts, allergies, and Meibomian gland disfunction (MGD). Some medications can also induce dry eyes, e.g., antihistamines, as well as some antidepressants and blood pressure medication (Wikipedia, "Dry Eye Syndrome").

Symptoms can include dryness, pain, blurred vision, fatigue, a feeling of dirt or something else in the eye, fluid or other discharge, headaches; itching, scratching, stinging, or other irritation; pressure, redness of the eyes, a scratchy sensation, sensitivity to light, and possibly scarring of the cornea (particularly without treatment), as well as other reported problems (National Institutes of Health, op. cit.; Wikipedia, op. cit.). Dry eye syndrome can affect five million diagnosed patients, and possibly as many as twenty million undiagnosed patients, in the United States alone. Worldwide, the problem might be significantly larger in scope.

Known methods of treating dry eyes include: hand application of "artificial tears," such as including saline accompanied by other substances included in tears, topically to the eye. Natural tears include a complex mixture of fatty oils, water, mucus, and more than 1500 different proteins, having at least three layers: (A) an outer oily lipid layer, produced by the Meibomian glands, which prevents tears from evaporating too quickly and maintains them on the eye; (B) a middle aqueous layer, produced by the lachrymal glands (i.e., tear ducts); and (C) an inner mucin layer, produced by goblet cells, which binds the aqueous layer to the eye (National Institutes of Health, op. cit.). Artificial tears generally contain a solution of substances intended to substantially mimic natural tears, such as saline and lubricants.

Other known methods include application of gels or ointments, reducing use of computer screens, and taking breaks from usage, application of warm or wet compresses, reducing or stopping smoking, limiting exposure to secondhand smoke, and certain prescription medication (e.g., cyclosporine, lifitegrast, restasis, or possibly corticosteroid eye drops for eye inflammation). Other known methods include stimulation of glands or nerves associated with tear production, as well as surgical procedures to temporarily or permanently reduce or eliminate drainage from the tear ducts (National Institutes of Health, op. cit.).

While these methods can generally treat of dry eyes that have become painful or irritating, they remain subject to several drawbacks. One problem with known methods is that dry eyes are often not identified as a problem until they have become painful or seriously irritating. For example, while excessive computer screen usage can cause the eyes to become tired, by the time the patient recognizes that their eyes have become tired, it is often too late to avoid the effect of dry eyes, and significant recovery time might be required. Another problem is that dry eyes might be caused by more than one source, prompting patients or medical personnel to discard a solution to one such source when their symptoms are not sufficiently alleviated. Another problem is that solutions to one set of causes might potentiate a different set of causes, prompting patients or medical personnel to employ solutions that actually make the problem worse.

Dry eyes conditions are sometimes also correlated with other deleterious medical conditions, such as migraine headaches, photophobia, damage to or degraded Meibomian glands, staining of ocular surfaces, sleep apnea or other degraded sleep quality, and other patient conditions that might be detected or monitored, predicted, and prevented or treated, or subject to patient self-care or other patient behavior, either in combination or conjunction with dry eyes.

Each of these issues, as well as other possible considerations, might cause difficulty in aspects of addressing the problems patients have with detecting and monitoring, predicting, preventing and treating, and training and rewarding patient self-care, with respect to dry eyes.

SUMMARY OF THE DISCLOSURE

This summary of the disclosure is provided as a convenience to the reader, and does not limit or restrict the scope of the disclosure or the invention. This summary is intended as an introduction to more detailed description found in this Application, and as an overview of techniques explained in this Application. The described techniques have applicability in other fields and beyond the embodiments specifically reviewed in detail.

This Application describes devices and techniques coupleable to a set of patient sensors, to an ambient environment, to external sensory input, and to a set of patient parameters determined (at least in part) in response to examination of the patient. The described devices and techniques can receive and maintain information in response thereto; and can correlate the received and maintained information with measures associated with detecting and monitoring, predicting, preventing and treating, and training and rewarding patient self-care and other patient behavior, with respect to dry eyes. The described devices and techniques can detect and monitor, predict, and prevent and treat (such as conducting treatment in real time), dry eyes and related conditions; and can train and reward patients to conduct self-care and other patient behavior with respect to dry eyes and related conditions, as well as other and further techniques.

In embodiments thereof, the described devices and techniques can monitor disease progression with respect to dry eyes and related conditions. In other embodiments, the described devices and techniques can collect information with respect to the patient sensors, the ambient environment, the external sensory input, or patient self-reports; and correlate that information with information with respect to dry eyes and related conditions. In other embodiments, the described devices and techniques can adjust external sensory inputs as part of their actions to perform to prevent or treat dry eyes; to influence patient behavior on the spot to prevent, treat, or ameliorate dry eyes; to train and reward patients to conduct self-care and other patient behavior with respect to dry eyes; or to train and reward patients for their alertness to dry eyes conditions and any correlated activities.

The described devices and techniques can also cooperate with other devices. Such other devices can include similar devices worn by nearby patients, such as to receive and maintain information about the ambient environment, or such as to communicate with medical personnel. Such other devices can also include medical devices for diagnosis or treatment, such as used by medical personnel to identify dry eyes conditions, to provide information so as to correlate conditions experienced by patients when medical personnel are not present. The described devices and techniques can adjust the parameters they use, such as in response to received information that differs from predictions, to provide superior behavior, and can communicate with other devices and with medical personnel in response thereto.

The devices and techniques can also be combined with devices and techniques disposed to perform similar functions with respect to other conditions, such as migraines, photophobia, neuro-opthalmic disorders, and other ocular conditions, such as with respect to combinations of dry eyes with other conditions. For example, the described devices and techniques can be combined with devices and techniques, such as those performed by medical personnel at medical offices, to generate professional tagging of dry eyes conditions. The described devices and techniques can use the professional tagging of dry eyes conditions to identify, alone or with other techniques, dry eyes conditions in real time. The described devices and techniques can maintain records of those dry eyes conditions in real time for use by medical personnel with other diagnostic or treatment devices at medical offices. For another example, the described devices and techniques can be combined with devices and techniques for treatment of sleep apnea or other sleep disorders, to identify REM (rapid eye movement) sleep conditions and their relation to one or more deleterious patient conditions.

This Application also describes use of digital eyewear, and other devices, with other and further techniques with respect to dry eyes.

BRIEF DESCRIPTION OF THE FIGURES

In the figures, like references generally indicate similar elements, although this is not strictly required. After reading this Application, those skilled in the art would recognize that the figures are not necessarily drawn to scale for construction, nor do they necessarily specify any particular location or order of construction.

FIG. 5 shows a conceptual drawing of an example communication system.

DETAILED DESCRIPTION

General Discussion

Figure 1:
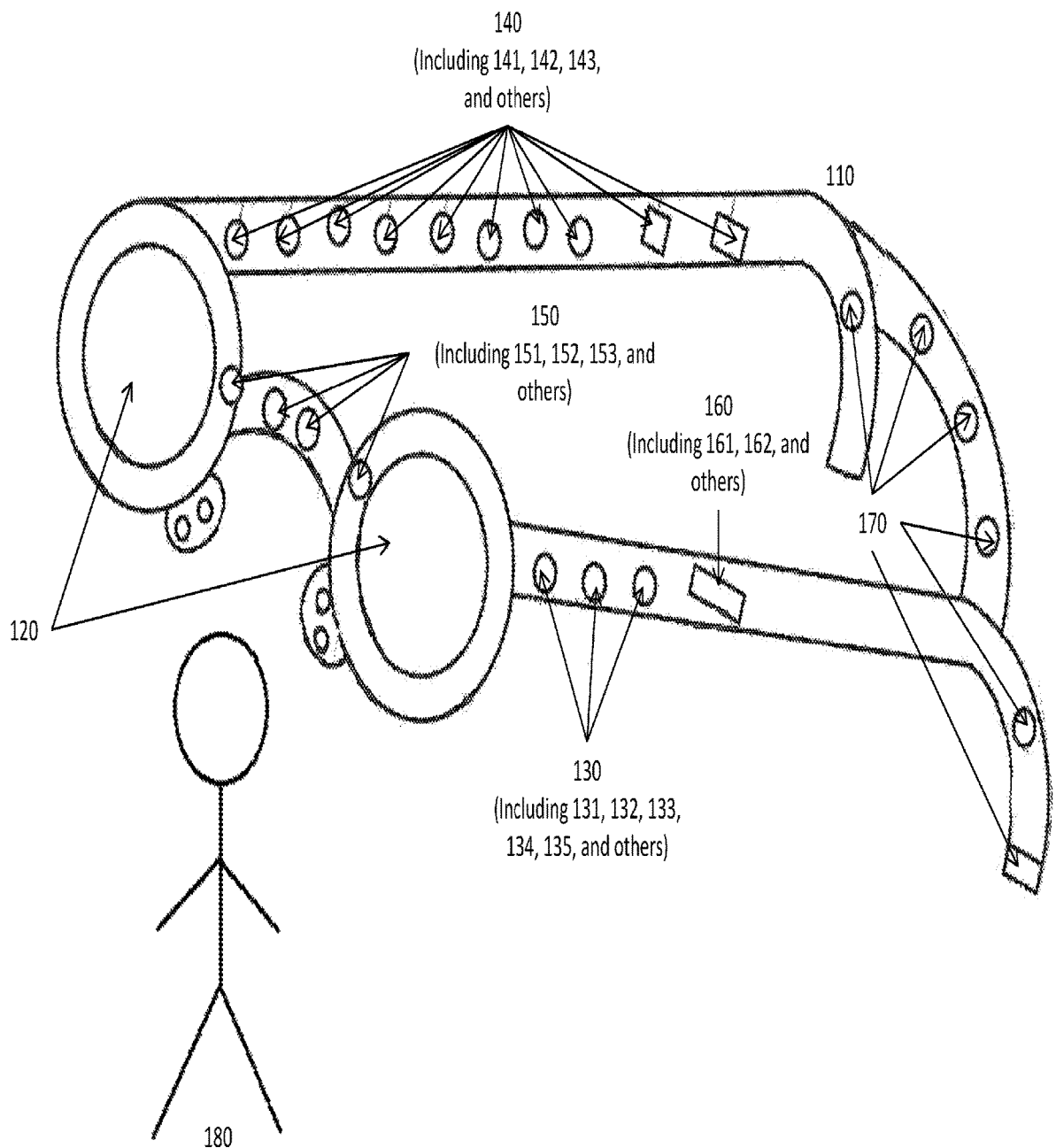
FIG. 1 shows a conceptual drawing of an example set of digital eyewear.

In one embodiment, devices and techniques can be coupled to a set of patient sensors, to an ambient environment, and to external sensory input. In one embodiment, the described devices and techniques can receive and maintain information about events including dry eyes (and effects resulting from dry eyes). The devices and techniques can detect or monitor (with or without patient assistance) whether the patient currently has dry eyes, and with what degree of severity. The devices and techniques can predict a likelihood (and associated timing or severity) of the patient suffering from dry eyes in the near future. The devices and techniques can conduct actions predicted to ameliorate, treat, or prevent dry eyes. The devices and techniques can direct the patient to self-treat the patient's dry eyes, and train the patient (such as using a reward procedure) with respect to such self-care and other patient behavior.

In one embodiment, the described devices and techniques can receive and maintain information from patient sensors, such as about conditions of the patient; from ambient sensors, such as about conditions of an ambient environment; and from external sensory inputs, such as those sensory inputs to be received (such as those which would be received if not intercepted) by the patient. The devices and techniques can use parameters correlating the received and maintained information with measures of likelihood (and associated timing or severity) of the patient suffering from dry eyes, either currently or in the near future, to determine those measures. Similarly, the devices and techniques can use parameters associating the received and maintained information with actions to perform to prevent or treat dry eyes. Similarly, the devices and techniques use parameters associating the received and maintained information with actions by which the patient can perform self-care (such as those patient actions beyond the scope of the devices and techniques themselves), and if performed, with actions to reward the patient for conducting self-care and possibly other patient behavior.

In one embodiment, the described devices and techniques adjust sensory inputs to be received by the patient, as part of their actions to perform to ameliorate, treat, or prevent dry eyes. The devices and techniques can also adjust the patient's sensory inputs to provide messages to the patient, such as to (A) warn the patient of actions to reduce the likelihood (or severity) of dry eyes occurring in the near term, (B) instruct the patient of actions to perform self-care with respect to dry eyes, and if performed, to reward the patient for conducting self-care and possibly other patient behavior.

In one embodiment, the described devices and techniques are disposed to cooperate with other devices, such as similar devices worn by nearby patients, to receive and maintain information about the ambient environment. Similarly, the devices and techniques can communicate with other devices; such as those associated with medical personnel, to inform them of the patient's condition, either on a continuing basis or in the event of relatively extreme cases; or with data repositories, such as to maintain records for later use in adjusting the parameters used for correlation.

In one embodiment, the described devices and techniques are disposed to adjust the parameters they use, such as in response to received information that differs from predictions. For example, when the devices or techniques determine that the patient is currently suffering from dry eyes, but the patient repeatedly denies symptoms thereof, the devices or techniques can adjust associated monitoring parameters (with respect to likelihood, severity, or both), and can send those adjusted parameters to other devices, such as (A) other nearby devices associated with other patients, (B) medical personnel, or (C) machine learning devices disposed to provide or adjust monitoring models with respect to dry eyes. The devices or techniques can similarly adjust parameters with respect to prediction, treatment/prevention, or self-care/training and other patient behavior.

Terms and Phrases

The phrase "digital eyewear", and variants thereof, generally refers to any device coupled to a wearer's input senses, including without limitation: glasses (such as those including lens frames and lenses), contact lenses (such as so-called "hard" and "soft" contact lenses applied to the surface of the eye, as well as lenses implanted in the eye), retinal image displays (RID), laser and other external lighting images, "heads-up" displays (HUD), holographic displays, electro-optical stimulation, artificial vision induced using other senses, transfer of brain signals or other neural signals, headphones and other auditory stimulation, bone conductive stimulation, wearable and implantable devices, and other devices disposed to influence (or be influenced by) the wearer.

The phrases "dry eyes", "dry eyes conditions", "dry eyes effects", and variants thereof, generally refer to any one or more portions of the cluster of symptoms associated with dry eyes, including as further described herein, as well as other effects associated with dry eyes, whether chronic or otherwise.

Figures and Text

Example Digital Eyewear

FIG. 1 shows a conceptual drawing of an example set of digital eyewear.

Lenses and Frames

A set of digital eyewear is described with respect to elements as shown in the figure, and as otherwise described herein, such as:

the digital eyewear 100;
an eyewear frame 110;
one or more lenses 120;
a set of patient sensors 130;
a set of ambient sensors 140;
a set of treatment devices 150;
an eyewear controller 160;
a set of input/output devices 170;
a patient 180 or other wearer (who is of course not part of the digital eyewear).

In one embodiment, the digital eyewear 100 can optionally include the eyewear frame 110, with the lenses 120, patient sensors 130, ambient sensors 140, treatment devices 150, eyewear controller 160, input/output devices 170, coupled thereto. The digital eyewear 100 can be disposed for coupling to the patient 180.

For example, the patient 180 can wear the eyewear frame 110. This can have the effect that the lenses 120 are disposed near the patient's (180) eyes, the patient sensors 130 are disposed near the patient's (180) eyes or otherwise near the patient 180, the treatment devices 150 are disposed near the patient's (180) eyes or otherwise near the patient 180, the input/output devices 170 are disposed convenient for use by the patient 180, and otherwise as described herein.

For another example, the digital eyewear 100 can be coupled, such as by a Bluetooth™ or other wireless connection to another wearable device (not shown), which can be worn by the patient 180 or by another wearer (not shown). Other wearable devices can include a wristband, such as a FitBit™, a glove, a headband, a necklace, one or more earrings, or other accessories, any of which can be worn by the patient 180 or another wearer. In such cases, the other wearer can include a family member, a caretaker, or medical personnel.

For another example, the digital eyewear 100 can be coupled to a mobile device (not shown), such as a cell phone, music player, or similar device, which can be carried or operated by the patient 180 or another user. For another example, the digital eyewear 100 can include or be coupled to one or more contact lenses, which can be worn by the patient 180 or other wearer. For another example, the digital eyewear 100 can include or be coupled to one or more implantable devices, such as an implantable lens (or replacement lens in the eye), a subcutaneous device, or one or more nanodevices or other devices suitable for operating inside the body, which can be coupled to the patient 180 or another user. For another example, the digital eyewear 100 can include or be coupled to an RID (retinal image display) such as a laser imaging device or otherwise.

In one embodiment, the lenses 120 are disposed under control of the eyewear controller 160 to possibly alter incoming external sensory input 121 (such as incoming light or UV) so that the patient 180 receives adjusted sensory input 122. For example, the adjusted sensory input 122 can be reduced in luminance (shaded), increased in luminance (inverse shaded), shaded/inverse-shaded with respect to particular frequencies, polarized/depolarized, or otherwise. The external sensory input 121 can be adjusted only with respect to particular locations in the patient's (180) viewing field, such as only where there is glare or shadow. Similarly, the adjusted sensory input 122 can present images to the patient 180 that are not otherwise present in the external sensory input 121, such as overlaid pictures, text, or messages to the patient 180.

Moreover, while this Application is primarily described with respect to attachment of the patient sensors 130, the ambient sensors 140, the treatment devices 150, and the eyewear controller 160, being coupled to the eyewear frame 110, in the context of the invention, there is no particular requirement for any such limitation. The patient sensors 130, the ambient sensors 140, the treatment devices 150, and the eyewear controller 160, can be disposed at other locations wherein they have the functions described herein, or similar functions, and can intercommunicate to exchange information. In such cases, patient sensors 130, the ambient sensors 140, the treatment devices 150, and the eyewear controller 160, can be coupled to the digital eyewear 100 as further described herein with respect to the lenses 120.

When devices supporting multiple digital eyewear 100 systems communicate, they can gather information about a greater area near the patient 170 (or a greater area near multiple such patients 170 or other users), can determine if the patient sensors 130 are detecting information unique to the patient 170 or shared by more than one patient 170, and can determine whether the ambient environment is affecting one patient 170 substantially more than others. As described herein, FIG. 5 shows a conceptual drawing of an example communication system.

In one embodiment, the input/output devices 170 can include elements as shown in the figure, and as otherwise described herein, such as:
one or more buttons, contacts, capacitive touch devices, or other haptic devices suitable to receive touch commands from the patient 180;
one or more microphones suitable to receive voice commands from the patient 180;
one or more cameras, motion sensors, or other detectors, suitable to receive motion commands from the patient 180.

In one embodiment, the devices suitable to receive touch commands, voice commands, or motion commands, can be coupled to a device other than the digital eyewear 100. For example, the touch command devices can include a smartphone or other mobile device, such as one having a capacitive touch screen, such as an iPhone™ or Android™ device. For another example, the voice command devices can also include a smartphone or other mobile device having a microphone. For another example, the motion command devices can include a smartphone or other mobile device having a camera. In such cases, the eyewear controller 160 can use information from the motion command devices to recognize gestures, sign language, facial expressions, and silent voice commands (using lip reading).

In one embodiment, the patient 180 includes a human being capable of recognizing dry eyes effects, such as a cognizant child, adolescent, or adult. However, in the context of the invention, there is no particular requirement for any such limitation. For example, the patient 180 can include a sedated patient or surgical patient (such as a patient disposed for ocular surgery or LASIK surgery), who might be temporarily unable to provide meaningful patient input. For another example, the patient 180 can include an infant or neonate, or other person not generally capable of providing meaningful patient input. For another example, the patient 180 can include an animal, such as a pet dog or cat.

Patient Sensors

In one embodiment, the patient sensors 130 can include at least one or more of the following:
a blink sensor 131;
a tear sensor 132;
an eye sensor 133;
a gaze detector 134;
an object detector 135;
patient sensors as further described in the Incorporated Disclosures.

In one embodiment, the blink sensor 131 can be disposed to conduct real-time detection of blinking by the patient 180. In such cases, the eyewear controller 160 can receive information from the blink sensor 131, and can include instructions to the computing device 161 by which the eyewear controller 160 can determine when the patient 180 blinks. In response to this information, the eyewear controller 160 (using its computing device 161) can determine a blink rate, that is, a frequency of blinks per minute; a blink intensity, that is, a speed of each blink. As further described herein, for each such patient feature, the eyewear controller 160 can also determine at least a first and second time-derivative, at least a first and second statistical moment, and at least a correlation between that parameter and any other feature the eyewear controller 160 determines.

For example, the blink sensor 131 can include a camera disposed with the patient's eye in its field of view; the blink sensor 131 can also include a computing device coupled to the camera, the computing device disposed to determine when and how frequently the patient's eyelid closes and re-opens. In such cases, the blink sensor 131 can determine whether the patient's blink is relatively complete, such as completely covering the pupil and causing the upper and lower eyelids to meet in the middle, or at least partially incomplete, such as leaving at least a portion of the pupil uncovered by blinking action, or otherwise failing to cause the upper and lower eyelids to meet in the middle.

In one embodiment, the tear sensor 132 can be disposed to conduct real-time measurement of the patient's (180) layers of tears, as further described herein, including for each layer, one or more of: a thickness, a density, a reflectivity, a capacitance, and possibly other features. For example, the tear sensor 132 can measure whether the patient's (180) lipid layer 311, aqueous layer 312, or mucin layer 313 (as further described with respect to FIG. 3) are too thick/thin, are not uniformly thick/thin with respect to the eye or are too different between the two eyes, are changing in thickness too rapidly or corresponding to some other feature, or are otherwise indicative of a possible problem. For example, if the patient's (180) lipid layer 311 is too thick/thin, it might be indicative of a problem with the patient's (180) Meibomian glands 321, that is, Meibomian gland disorder (MGD). For another example, if the patient's (180) aqueous layer 312, is too thick/thin, it might be indicative of a disorder of the lachrymal glands 322.

In such cases, the tear sensor 132 can provide that information to the eyewear controller 160, which can predict/avert dry eyes effects (or detect/treat those effects if they have already occurred), can send that information to one or more recipients, or can otherwise act on that information.

In one embodiment, the eye sensor 133 can be disposed to conduct real-time evaluation of the patient's (180) eyes, including for each eye, one or more of: the sclera, the pupil, the lens, the eyelash, the eyelid, and possibly other features. For example, the eye sensor 133 can include a camera (whether infrared, visible, ultraviolet, or operative in other electromagnetic frequencies), an ultrasonic sensor (such as can be reflected from one or more portions of the eye, or another sensor. In response thereto, the eye sensor 133 can obtain a still/video image of at least a portion of the eye, such as a still/video image of one or more of: a surface of the eye, a tear duct.

Similar to the tear sensor 132, the eye sensor 133 can provide that information to the eyewear controller 160, which can predict/avert dry eyes effects (or detect/treat those effects if they have already occurred), can send that information to one or more recipients, or can otherwise act on that information.

In one embodiment, the gaze sensor 133 and the object detector 134 can operate to determine an object the patient 180 is looking at or focusing on. For example, the patient 180 might be looking at, or focusing on, a computer screen or a mobile device screen. If this condition continues for too long, the patient 180 might become subject to a dry eyes effect. For another example, the patient 180 might be looking at, or focusing on, a scene having excessive glare. If this condition continues for too long, the patient 180 might become subject to a dry eyes effect. For another example, the patient 180 might be looking at, or focusing on, a relatively distant scene. This can alleviate the likelihood or severity of a dry eyes effect, particularly if the patient 180 has otherwise normal activity of their lachrymal glands, tear ducts, and Meibomian glands.

Similar to the tear sensor 132 and the eye sensor 133, the gaze sensor 133 and the object detector 134 can provide that information to the eyewear controller 160, which can predict/avert dry eyes effects (or detect/treat those effects if they have already occurred), can send that information to one or more recipients, or can otherwise act on that information.

Ambient Sensors

In one embodiment, the ambient sensors 140 can include at least one or more of the following:
  a luminosity detector 141;
  an atmospheric sensor 142;
  a location sensor 143;
  ambient sensors as further described in the Incorporated Disclosures.

In one embodiment, the luminosity detector 141 can measure, in real-time, an amount of infalling light on each eye. For example, the luminosity detector 141 can measure a total light intensity. For another example, the luminosity detector 141 can measure a total light intensity in a selected frequency range (such as ultraviolet light or blue light).

In one embodiment, the atmospheric sensor 142 can measure, in real-time, atmospheric and weather conditions, such as one or more of: atmospheric pressure and relative humidity, temperature and wind-chill factor, and a measure of atmospheric pollution (such as ionization, particulates, or amount of $SO_2$ or other pollutant).

Similar to the patient sensors 130, the ambient sensors 140 can provide their information to the eyewear controller 160, which can predict/avert dry eyes effects (or detect/treat those effects if they have already occurred), can send that information to one or more recipients, or can otherwise act on that information.

In one embodiment, the location sensor 143 can determine, in real-time, a place where the patient 180 is located. For example, the location sensor 143 can include a GPS detector or other device capable of electromagnetic determination of the patient's (180) location. In such cases, the eyewear controller 160 can communicate with a data repository 191 (as further described with respect to FIG. 5) to obtain information with respect to a set of allergens then present in the atmosphere. Allergens are believed to be relatively localized; this can have the effect that the eyewear controller 160 can determine with relative confidence which allergens are present and possibly affecting the patient 180.

Treatment Devices

In one embodiment, the treatment devices 150 can include at least one or more of the following:
  a blink substitution device 151;
  an alerting device 152;
  a rewarding device 153;
  treatment devices as further described in the Incorporated Disclosures.

In one embodiment, the blink substitution device 151 can be disposed to treat the patient 180 for a dry eyes condition, such as on the patient's (180) eye. For example, the treatment device 151 can include a wetting device 151*a*, an air puff device 151*b*, a mild shock device 151*c*, a key substitution device 151*d*, or another device disposed to relieve the dry eyes condition.

For example, the blink substitution device 151*a* can include a reserve tank (not shown) and an aerosolizer (not shown). When the digital eyewear 100 includes glasses frames, the reserve tank can be coupled to the glasses frames. Alternatively, when the digital eyewear 100 includes a contact lens 120 or an implanted lens 120, the reserve tank can be embodied in the lens 120 itself, or disposed on or near the lens 120, or coupled to the lens 120 so that the substance to be aerosolized is accessible to the lens 120.

In such cases, the reserve tank can include one or more of: water, saline, artificial tears, oil, a medicated compound such as including a medication known to prevent/treat dry eyes effects (such as the medication "restasis"), a topical or other pain reliever, or another substance suitable for preventing/treating dry eyes effects. When the digital eyewear 100 includes more than one such reserve tank, a first reserve tank can include a first such substance and a second reserve tank can include a second such substance.

For example, the air puff device 151*b* can include a nozzle (not shown) disposed to direct a puff of air, or another gas, gently at the patient's (180) eye, prompting the patient 180 to blink. When the patient 180 blinks, the natural effect of releasing tears wets the surface of the patient's (180) eye, with the effect that the dry eyes condition should be alleviated. The nozzle can be disposed near a surface of the patient's (180) eye, so as to direct the puff of air directly onto the surface of the eye without substantial dissipation and without having any substantial likelihood of damaging the eye. In such cases, the gas can include one or more of: air, a chemically neutral gas such as carbon dioxide, or a mildly toxic gas such as nitrous oxide (so as to prompt the patient 180 to blink with a relatively lesser amount of pressure).

For example, the mild shock device 151c can include an electrical or electronic circuit disposed on or near the patient's (180) eye, or on or near a muscle disposed to cause the patient 180 to blink. The circuit can prompt the muscle to tense; this can have the effect that the patient's (180) eyelid blinks. As further described above, when the patient 180 blinks, the natural effect of releasing tears wets the surface of the patient's (180) eye, with the effect that the dry eyes condition should be alleviated. The circuit can be disposed to impart one or more of: a mild electrical shock, a mild electrical charge causing irritation or otherwise prompting the patient 180 to blink, a capacitive charge (such as might be received by a contact lens or otherwise by the surface of the eye) causing irritation or otherwise prompting the patient 180 to blink, another electromagnetic effect prompting the patient 180 to blink, or otherwise.

For example, the key substitution device 151d can include a coupling between the digital eyewear 100 and an external device (not shown), such as a television controller, a computer input device, a smartphone or other mobile device, a game controller, an automobile control system, another device ordinarily controlled by hand (such as using a keyboard or a pointing device), or otherwise. In such cases, the key substitution device 151d can require the patient 180 to blink periodically, or otherwise from time to time, by disabling one or more controls to the external device (not shown), and substituting recognition of the patient's (180) blink as triggering that input.

In such cases, the key substitution device 151d can require the patient 180 to blink by substituting the patient's (180) blink for one or more of:
- a television control that changes the channel or alters the volume, any other frequently used control, or any other selected control element;
- a computer input control such as a "control" key, a "return" key, a space bar, any other frequently used key, or any other selected key;
- a smartphone input control such as a "make call" command, or one or more of the keys described with respect to the computer input control;
- a game controller input such as a jumping or shooting button, an "A" button, a "B" button, or one or more of the keys described with respect to the computer input control;
- or other commands or controls as appropriate to the particular device.

Since the patient 180 who is using a television, or a computer, or a smartphone or other mobile device, or a game controller, would likely make frequent use of the selected key or control, the patient 180 would be required to blink more frequently to use those selected keys or controls. This can have the effect that the key substitution device 151d can prompt the patient 180 to blink more frequently than otherwise associated with use of that device.

Alternatively, the key substitution device 151d can require the patient 180 to blink when using other types of external device. For example, when the patient 180 is driving an automobile or other vehicle, it might occur that the patient 180 blinks less often than desirable due to road glare or excessively sunny weather. In such cases, the key substitution device 151d can require the patient 180 to blink by substituting the patient's (180) blink for control of the vehicle's radio, lights, accelerator, brakes, steering wheel, or otherwise.

In one embodiment, the alerting device 152 can be disposed to warn the patient 180 of a likely impending dry eyes effect, such as when the eyewear controller 160 determines that the patient 180 is relatively likely to suffer a near-term dry eyes effect. For example, if the patient 180 has been staring at a computer screen for a relatively long time, the eyewear controller 160 can trigger the alerting device 152 when that long time exceeds a selected threshold. The eyewear controller 160 can select the threshold in response to the patient's (180) history with dry eyes effects, in response to medical knowledge, in response to the speed of onset of the dry eyes effect, in response to the patient's (180) history of response to the alerting device 152, or other relevant factors.

For example, the alerting device 152 can be disposed to frequently and periodically, or otherwise from time to time, present the patient 180 with a "heads-up" display (HUD), or other augmented reality presentation, informing the patient 180 of their blink rate and other blink-related behavior. The HUD can take the form of a histogram of blink delays, an X-axis showing an amount of time and a Y-axis showing a number of blinks. The HUD can take the form of a clock showing a time to next desired blink, either with a digital countdown or with a sweep second to a next desired blink. The HUD can also take the form of a color indicating whether the patient 180 is blinking sufficiently frequently. The HUD can also take the form of a request to the patient 180, to blink or to use eye drops, when the patient 180 is otherwise not blinking sufficiently frequently. By frequently presenting the patient 180 with actionable information about when to blink and how well the patient 180 is performing with respect to blinking, the patient 180 can be encouraged to blink at a desired rate, or at least at a more frequent rate.

In such cases, the alerting device 152 can provide a "YELLOW ALERT", such as a light buzzing sound, light musical chime, or other relatively unobtrusive indicator, when the likelihood of a near-term dry eyes effect exceeds a first selected threshold. For example, the yellow alert (not shown) can be triggered when the patient 180 has a blink rate of less than about 8 blinks per minute, or another value in response to the ambient sensors 130 or the patient's history. For example, the yellow alert (not shown) can provide a first warning to the patient 180 to take action to avert the impending dry eyes effect. For example, the yellow alert can be coupled with a relatively unobtrusive suggestion, such as a message to the patient 180 in an unobtrusive corner of the patient's (180) adjusted sensory input 122, of one or more ways to avert the impending dry eyes effect. In such cases, the patient 180 will hopefully take the hint and take action.

In such cases, the alerting device 152 can provide a "RED ALERT", such as a more insistent buzzing sound, louder musical chime, or other less ignorable indicator, when the likelihood of a near-term dry eyes effect exceeds a first selected threshold. For example, the red alert (not shown) can be triggered when the patient 180 has a blink rate of less than about 3 blinks per minute, or another value in response to the ambient sensors 130 or the patient's history. For example, the red alert (not shown) can provide a second warning to the patient 180 to take action to avert the impending dry eyes effect. For example, the red alert can be coupled with a more insistent suggestion, such as a message overlaid on a more obtrusive portion (such as a central location) of the patient's (180) adjusted sensory input 122.

Similar to the yellow alert, the message can suggest, possibly more insistently, one or more ways to avert the impending dry eyes effect. In such cases, the patient 180 will hopefully take the hint and take action.

In alternative embodiments, in addition to activating the alerting device 152, the eyewear controller 160 can maintain the yellow alert or the red alert until the patient 180 reaches an acceptable blink rate. For example, an acceptable blink rate can be more than 15 blinks per minute, or another value in response to the ambient sensors 130 or the patient's history. When the acceptable blink rate is reached, the eyewear controller 160 can cancel the yellow alert or the red alert. Alternatively, when a sufficient blink rate is reached, the eyewear controller 160 can replace the red alert with a (less urgent) yellow alert.

In alternative embodiments, in addition to or in lieu of activating the alerting device 152 with a red alert, the eyewear controller 160 can immediately provide treatment for the dry eyes effects, using one or more of the blink substitution devices 151. In such cases, the eyewear controller 160 can proceed directly to wetting the patient's (180) eye using one or more of: aerosolized "artificial tears," (possibly including any product marketed using the phrase "artificial tears," or any product marketed for alleviation of dry eyes effects, or any combination thereof) eye drops, oil, saline, water, or medication such as the medication "restasis"; directing an air puff at patient's (180) eye; or prompting the patient's (180) eye to blink using a mild electrical shock or charge. When the digital eyewear 100 includes an eyewear frame 110, the treatment devices 150 can be mounted on the frame, or otherwise near the patient's (180) eye. When the digital eyewear 100 includes a contact lens 120 or is mounted in the lens of the patient's (180) eye itself, the treatment devices 150 can be mounted within the lens 120 and be triggered by an electromagnetic or ultrasound signal, can be received by the contact lens or the eye's lens using a capacitive effect, or can otherwise be coupled to the digital eyewear 100.

In one embodiment, the rewarding device 153 can provide a reward to the patient 180 in the event that the patient 180 has taken the suggested action to avert the impending dry eyes effect (or to ameliorate a current dry eyes effect). For example, the rewarding device 153 can provide one or more of the possibilities described at the step 465 with respect to FIG. 4. For another example, the rewarding device 153 can provide the patient 180 with at least some of the information described herein with respect to the HUD, so as to apprise the patient 180 of how well they have responded to suggested actions, and so as to maintain the patient 180 aware of their eye health with respect to dry eyes conditions and effects.

Eyewear Controller

In one embodiment, the eyewear controller 160 can include elements as shown in the figure, and as otherwise described herein, such as:
  a computing device 161;
  a communicator 162;
  elements as further described in the Incorporated Disclosures.

In one embodiment, the computing device 161 can include a processor, program and data memory, and input/output elements coupled to the patient sensors, the ambient sensors, and the treatment devices. The communicator 162 can include a sending/receiving element, suitable for sending/receiving messages (not shown) to and from external devices 190. As further described herein, the external devices 190 can include a data repository 191, medical personnel 192, devices having other functions described herein, or otherwise.

In one embodiment, the gaze detector 163 can determine a gaze direction and focal length for each eye. Although the gaze direction and focal length of the left eye and right eye should match, this is not necessarily so. The gaze detector 163 can also be disposed to determine, such as in combination with the object detector 164, information from which the eyewear controller 160 (using the computing device 161) can determine an object upon which the patient 180 is focusing. For example, the gaze detector 163 and the object detector 164 can be disposed to determine whether the patient 180 is focusing on one or more of:
  a television screen;
  a computer screen;
  a gaming console;
  a smartphone or other mobile device screen;
  another person;
  another nearby object;
  a distant object, horizon, or sky;
  a beach scape, a snow scape, or a water surface such as a lake or sea surface; or one or more other objects or images.

As further described herein, the eyewear controller 160 can determine, such as in combination with the patient sensors 130 and the ambient sensors 140, and using information from the gaze detector 163 and the object detector 164, whether the patient 180 is focusing in a manner likely to induce a dry eyes effect. For example, if the patient 180 stares at a computer screen or a mobile device screen for hours, the eyewear controller 160 can conclude that the patient 180 is likely to suffer a dry eyes effect. For another example, if the patient 180 stares into a bright light or a region having glare for too long, the eyewear controller 160 can conclude that the patient 180 is likely to suffer a dry eyes effect.

Example Eyewear Lenses

Figure 2:
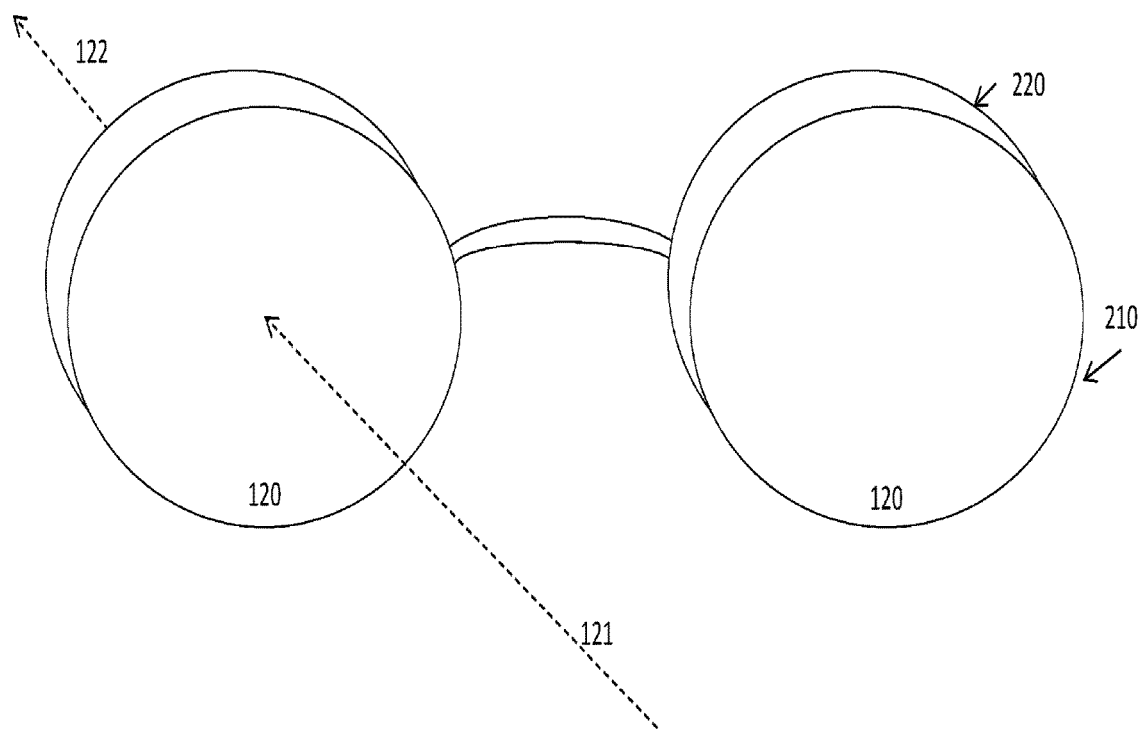
FIG. 2 shows a conceptual drawing of an example set of eyewear lenses.

FIG. 2 shows a conceptual drawing of an example set of eyewear lenses.

In one embodiment, the lenses 120 can include elements as shown in the figure, and as otherwise described herein.

The lenses 120 can include a left-eye lens disposed to present information to the patient's left eye, and a right-eye lens disposed to present information to the patient's right eye. The lenses 120 can be disposed to present information in one or more ways.

For a first example, the lenses 120 can include a substantially transparent element disposed to allow passage of light from the external sensory input 121. In such cases, the transparent element can be controlled to block passage of some or all of the light into the eye from specified locations (such as pixels). Similarly, in such cases, the transparent element can be controlled to allow passage of some or all of the light for the entire lens. In such cases, the transparent element can be controlled to allow passage of light at specified frequencies (such as ultraviolet light, blue light, or otherwise). Moreover, the transparent element can be controlled to allow or emit light into the eye from specified locations (such as pixels) and at specified frequencies (such as green light).

This can have the effect that the lenses 120 adjust the external sensory input 121 to provide the adjusted sensory input 122 to the patient 180, as controlled by the eyewear controller 160. This can have the effect that the eyewear controller 160 can reduce or increase the intensity of the external sensory input 121, reduce or increase the intensity of selected frequencies in external sensory input 121, replace selected frequencies in external sensory input 121, with distinct other frequencies, and replace the external sensory input 121 with the adjusted sensory input 122. When the eyewear controller 160 provides the adjusted sensory input 122, it can alter all of the external sensory input 121, or only a selected portion thereof.

For a second example, the lenses 120 can include a substantially opaque element disposed to block and measure incoming light from external sources, wherein the eyewear controller 160 can identify the external sensory input 121, without necessarily allowing that external sensory input 121 to reach the patient's (180) eye. The substantially opaque element can include, or alternatively be paired with, a mirror or screen at which the eyewear controller 160 can direct light so as to be reflected into the patient's (180) left eye, patient's (180) right eye, or both.

This can have the effect that the lenses 120 provide the adjusted sensory input 122 to the patient 180, modified as desired by the eyewear controller 160. In such cases, this can have the effect that the eyewear controller 160 can provide the adjusted sensory input 122 in place of the entire external sensory input 121, or only a selected portion thereof, as described with respect to the first example. The mirror or screen does not need to be collocated with the lenses 120. For example, they can instead be disposed as in a retinal image display. This can have the effect that the eyewear controller 160 can emit light directly into the eye, such as from a laser or a filtered white light source.

In one embodiment, the lenses 120 can include multiple digital lenses, multilayered lenses or multi-coated lenses, such as one or more of the following:

a first layer 210, including one or more of: a lens, a lens layer, or a lens coating;

a second layer 220, including one or more of: a lens, a lens layer, or a lens coating;

other elements as further described in the Incorporated Disclosures.

In one embodiment, each of the first layer 210 and the second layer 220 can be static (that is, having a substantially constant effect) or electrodynamic (that is, responsive to an electromagnetic or other control signal).

In one embodiment, the first layer 210 can include an anti-reflective effect responsive to selected frequencies of electromagnetic radiation, with the effect of reducing a selected electromagnetic frequency (such as blue light, ultraviolet A or B radiation, or otherwise).

In one embodiment, the second layer 220 can include a shading effect, possibly responsive only to an intensity of electromagnetic radiation (that is, monochrome), or alternatively responsive to selected frequencies of electromagnetic radiation, with the effect of shading/inverse-shading. For example, the second layer 220 can include a fast-acting adaptive shading element (such as using LCD or other techniques) and can be disposed for relatively rapid control of light intensity. For another example, the second layer 320 can include an adaptive electrochromatic effect, with the effect that it can be disposed either (a) in a clear state, or (b) in a filtering state in which is allows selected frequencies (such as a specific color of light, such as green light) to pass through to the patient's eye.

In one embodiment, the combination of the first layer 210 and the second layer 220 can be disposed both (a) to remove rapid bursts of light, and (b) remove dangerous frequencies of light, while still allowing passage of valuable frequencies of light.

In one embodiment, the lenses 120 can include eyeglass lenses (such as those disposed in an eyeglass frame, and generally disposed between the eye and external images), contact lenses (such as those disposed on the surface of the eye, and generally disposed to cover the pupil with respect to external images), implantable lenses (such as those disposed below the surface of the eye, or to replace the natural lens of the eye, and generally disposed to interpose between the retina and external images), or otherwise.

In one embodiment, the lenses 120 can be disposed between the patient's vision and the external sensory input 121 infalling from in front of the patient 180, infalling from the peripheral vision (side to side) of the patient 180, and infalling from between the patient's (180) vision and other directions (such as from above, from below, and from behind such as reflecting off the eyeware frame 110 or the lenses 120 themselves).

Patient Eye Features

Figure 3:
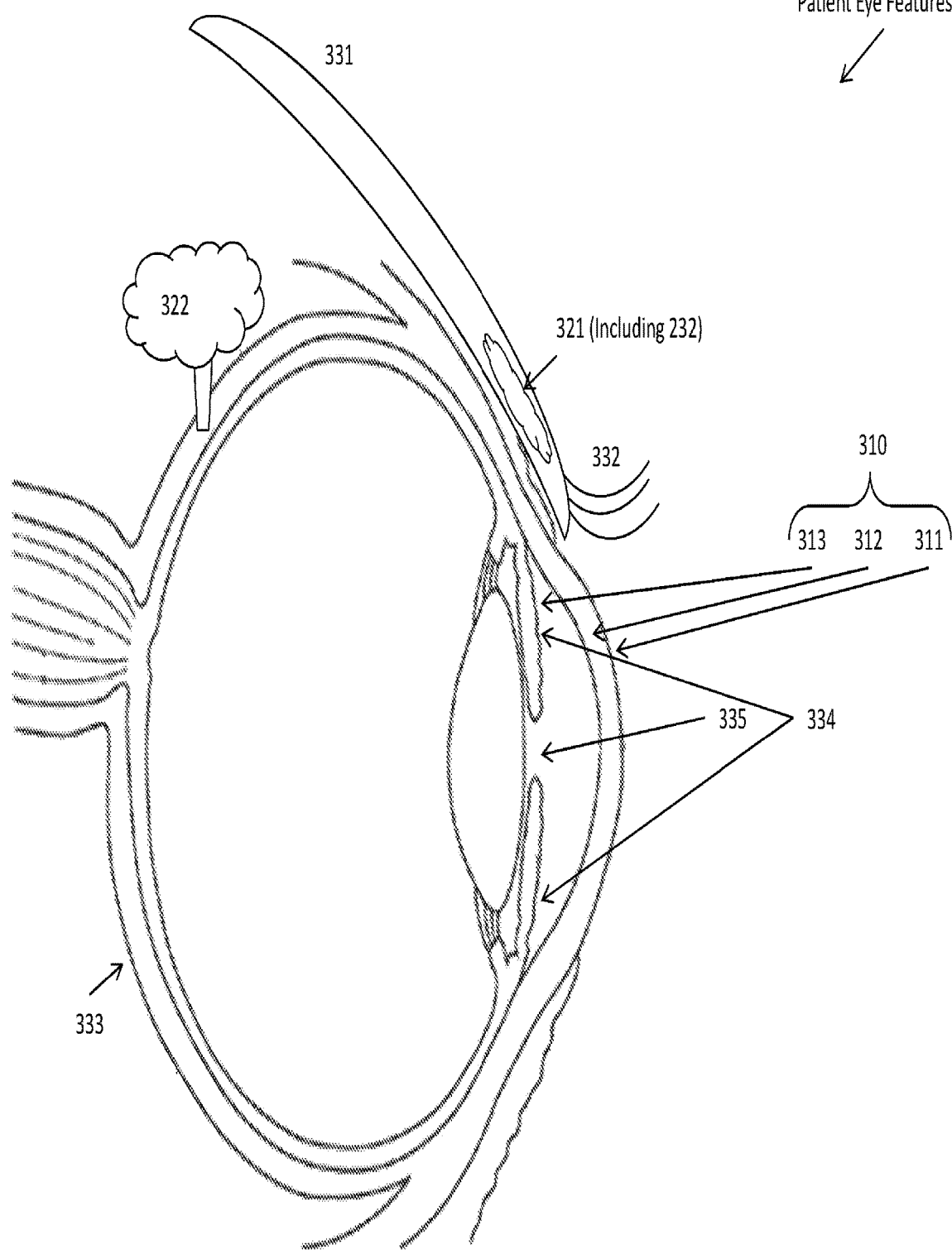
FIG. 3 shows a conceptual drawing of an example set of patient eye features.

FIG. 3 shows a conceptual drawing of an example set of patient eye features.

The patient's (180) eye features 300 can include elements as shown in the figure, and as otherwise described herein, such as one or more of:

a tear film 310;

a lipid layer 311, an aqueous layer 312, a mucin layer 313;

a set of Meibomian glands 321, a set of lachrymal glands 322, a set of goblet cells 323;

a pair of eyelids 331, an eyelash 332, a sclera 333, an iris 334, a pupil 335;

other features as further described in the Incorporated Disclosures.

In one embodiment, the tear film 310 includes the lipid layer 311, produced by the Meibomian glands 321; the aqueous layer 312, produced by the lachrymal glands 322; and the mucin layer 313, produced by the goblet cells 323. The mucin layer 313 generally binds the tear film 310 to the surface of the eye, including the sclera 333, the iris 334, and the pupil 335. The aqueous layer 312 is coupled to the mucin layer 313, and generally provides the "wetting" effect of the tear film 310. The lipid layer 311 prevents the aqueous layer 312 from too-rapid evaporation into the atmosphere.

Methods of Operation

Methods of operation can include steps as described herein. While the steps are shown and described in a linear order, in the context of the invention, there is no particular requirement for any such limitation. Except where explicitly stated, there is no particular requirement for the steps to be encountered or performed linearly, or in any particular order or by any particular device. For example and without limitation, the steps can be encountered or performed in parallel, in a pipelined manner.

One or more portions of the methods are sometimes described as being performed by particular elements of the systems described herein, or sometimes by the method itself. When a flow point or method step is described as being performed by the method, it can be performed by one or more of those elements, by one or more portions of those elements, by an element not described with respect to the figure, by a combination or conjunction thereof, or otherwise.

Detection and Treatment of Dry Eyes

Figure 4:
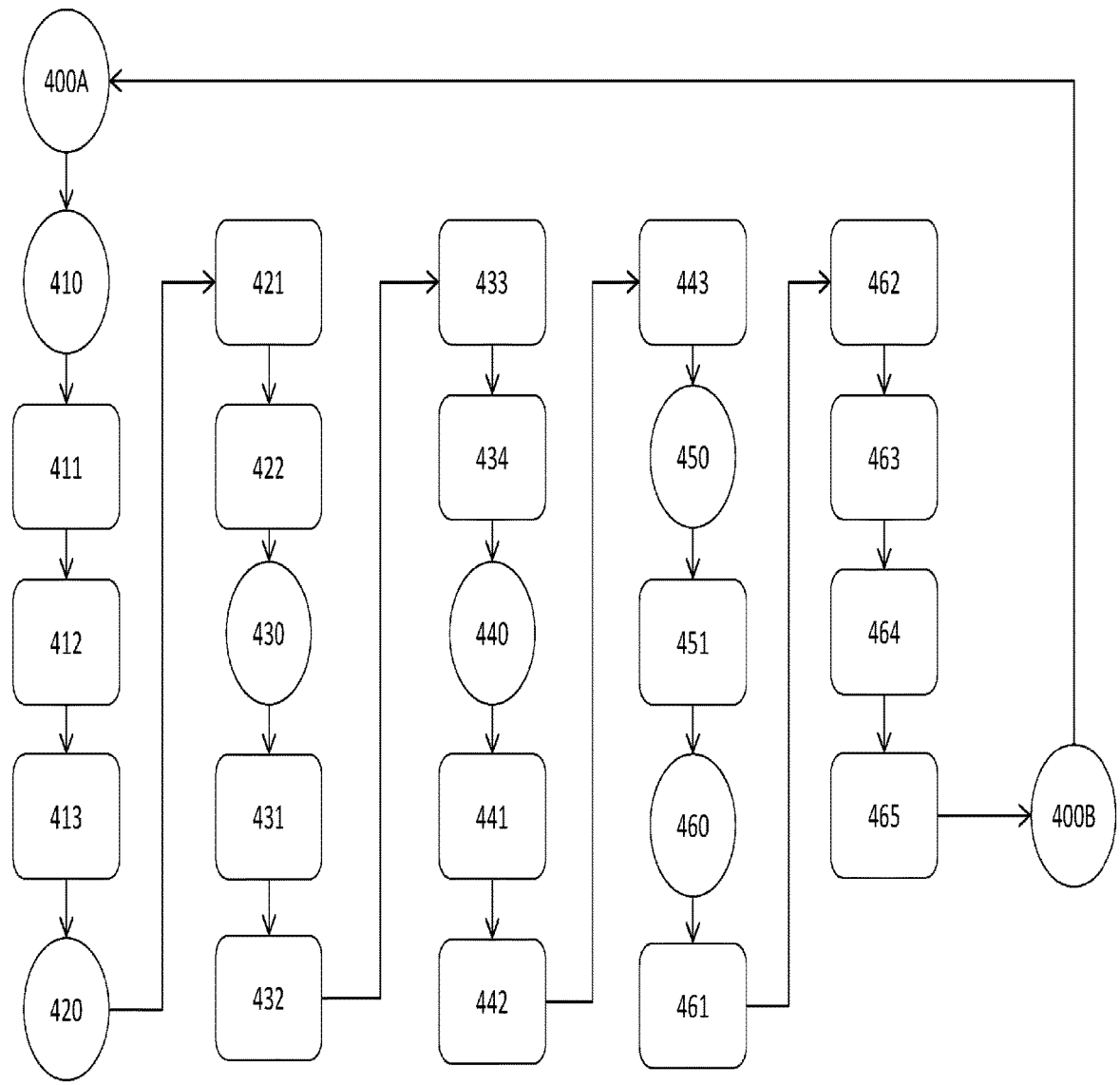
FIG. 4 shows a conceptual drawing of a first example method of operation.

FIG. 4 shows a conceptual drawing of a first example method of operation.

A method 400 includes flow points and method steps as shown in the figure, and as otherwise described herein, such as:

a flow point 400A, in which the method 400 is ready to begin;

a flow point 400B, in which the method 400 is ready to finish.

A flow point 400A indicates that the method 400 is ready to begin.

The method 400 can be triggered by one of more of the following:

a patient input (or signal from an input/output device 170) requesting that the method 400 is started;

a passage of time, such as from a last time the method 400 was started or the last time the method 400 was finished;

a message from an external device 190 or from medical personnel 192;

an alert or signal from one or more of the patient sensors 130 or ambient sensors 140;

or as otherwise described herein.

The method 400 initiates operations and starts/restarts any operations that are necessary or convenient. For example, when using an electronic controller, the controlling device allocates and possibly initializes useful storage values. The method 400 performs any initiating routines, and where applicable, transfers power control to an operational mode.

Monitoring Dry Eyes Effects

A flow point 410 indicates that the digital eyewear 100 is ready to monitor patient sensors 130 and ambient sensors 140.

At a step 411, the digital eyewear 100 receives direct information from the patient sensors 130 and ambient sensors 140. Similar to the method described in the Incorporated Disclosures, the eyewear controller 160 can determine derivative information with respect to that direct information, such as at least first and second time-derivatives thereof, at least first and second statistical moments thereof, and such as correlations between that information and any other information available to the digital eyewear 100.

At a step 412, similar to the method described in the Incorporated Disclosures, the digital eyewear 100 collects a set of history information from the patient sensors 130 and ambient sensors 140, the treatment devices 150, and patient self-reports of dry eyes. As noted with respect to the just-previous step, the eyewear controller 160 can determine correlations using that history information.

At a step 413, similar to the method described in the Incorporated Disclosures, the digital eyewear 100 exchanges the history information with one or more data repositories 191. In one embodiment, medical personnel, such as at a ophthalmologist's or optometrist's office, can determine a set of baseline information, or the patient 180 can collect information independently for a period of time.

In one embodiment, similar to the method described in the Incorporated Disclosures, the patient can self-report on dry eyes by using an input device on the digital eyewear 100, or by using a smartphone app on a mobile device (not shown) that is coupled to one of the communicators 162 on the digital eyewear 100. Patient input can be patient-initiated or can be in response to a request for information from the digital eyewear 100. As part of this step, the digital eyewear 100 can use its communicator 162 to exchange messages with a smartphone app on a mobile device, such as to obtain information from the patient 180.

The method proceeds with the next flow point.

Detecting Dry Eyes Effects

At a flow point 420, similar to the method described in the Incorporated Disclosures, the digital eyewear 100 is ready to detect whether the patient is suffering from dry eyes (a "dry eyes effect").

At a step 421, similar to the method described in the Incorporated Disclosures, the digital eyewear 100 can detect whether the patient is suffering from a dry eyes effect, either in response to patient input (as described herein), or in response to information from patient sensors 130.

In one embodiment, similar to the method described in the Incorporated Disclosures, the digital eyewear 100 determines only a likelihood of a dry eyes effect. For example, the eyewear controller 160 can be responsive to a set of input parameters, and can determine from those input parameters a likelihood of a dry eyes effect. In such cases, the digital eyewear 100 can determine a measure of likelihood, such as either a numerical probability estimate, or a bucketed probability estimate of the form "very likely," "likely," "somewhat likely," or "relatively remote."

In such cases, similar to the method described in the Incorporated Disclosures, the eyewear controller 160 can give substantial weight to the patient's assessment of dry eyes, but there is no special requirement to take the patient's assessment as conclusive. The patient 180 might have erroneously tapped an input button indicating dry eyes, or the patient 180 might have inaccurately concluded that momentary scratchiness was a dry eyes effect. Absent evidence otherwise, the eyewear controller 160 can use the patient's assessment as an indicator to adjust its own predictive parameters, as described herein.

In one embodiment, similar to the method described in the Incorporated Disclosures, the digital eyewear 100 can determine a likelihood of whether the patient is suffering from a dry eyes effect, in response to blink rate and other factors described herein. For example, as further described herein, a slow blink rate; a constant focus on a distance associated with a television screen, computer screen, or smartphone screen; or a measure associated with lack of an adequate tear film; can each be correlated with dry eyes.

In one embodiment, to determine whether the patient is suffering from a dry eyes effect, the eyewear controller 160 can be responsive to one or more of the following. Similar to the method described in the Incorporated Disclosures, each of the following can include the direct measurement, at least first and second time-derivatives thereof, at least first and second statistical moments thereof, and such as correlations between that information and any other information available to the digital eyewear 100.

With respect to patient sensors 130, the digital eyewear 100 can consider at least the following:

a blink rate (frequency of blinks per minute), a blink intensity (speed of blink);

a focal length of the eye, a difference between focal lengths of two eyes;

an object at which the eye gaze is directed;

for each of the layers of tears, a thickness, a density, a reflectivity, a capacitance;

a still or video image of at least a portion of the eye (sclera, pupil, lens, eyelash, eyelid, or otherwise);

a still or video image of at least a portion of a tear duct;

other indicators of dry eyes effects.

For example, the digital eyewear 100 can consider the blink rate of the patient 180. When the patient 180 is viewing a computer screen or a mobile device screen, blink rate can decrease from a normal rate of about 20 blinks/minute to as low as 2 blinks/minute. At only 2 blinks/minute, the patient 180 might have a serious risk of incurring a dry eyes effect.

For another example, the digital eyewear 100 can consider the blink rate of the patient 180. When the patient 180 blinks very quickly after a relatively long period without blinking, this might be an indicator that the patient 180 feels their eyes are dry or scratchy, or is otherwise suffering a dry eyes effect.

For another example, the digital eyewear 100 can consider the focal length of the eye, as well as and possibly in conjunction with an object at which the patient 180 is looking. When the patient 180 is looking at a computer screen or a mobile device screen, the patient 180 is more likely to incur a dry eyes effect. Accordingly, the digital eyewear 100 can determine whether the patient 180 is looking at a computer screen or a mobile device screen, and determine a likelihood of a near-term or current dry eyes effect in response thereto. The digital eyewear 100 might take into account whether the patient 180 has myopia/presbyopia or astigmatism, as possibly indicated by use of prescription lenses.

For another example, as further described herein, the digital eyewear 100 can consider information about each layer of the patient's (180) tears. As further described herein, information about each layer of the patient's (180) tears might be probative of a likelihood of a near-term or current dry eyes effect. This might include information about thickness, density, reflectivity, capacitance, or other measures of each layer of the patient's (180) tears, as well as their progress over time. This might also include information about tear film formation or breakup, and related information.

For another example, as further described herein, the digital eyewear 100 can consider a still/video image of at least a portion of the patient's (180) eye, tear duct, or other anatomical feature. For example, if a still/video image of the patient's (180) sclera indicates a current or incipient ocular ulcer, the digital eyewear 100 can consider that information when determining the likelihood of a near-term or current dry eyes effect. For another example, if a still/video image of the patient's (180) eyelash or eyelid indicates the presence of dirt or grit, the digital eyewear 100 can consider that information as well when determining the likelihood of a near-term or current dry eyes effect. For another example, if a still/video image of the patient's (180) tear duct indicates the growth of a sty, the digital eyewear 100 can consider that information as well when determining the likelihood of a near-term or current dry eyes effect.

With respect to ambient sensors 140, the digital eyewear 100 can consider at least the following:
- a total light intensity;
- a light intensity in a selected frequency range (e.g., ultraviolet, blue);
- a local temperature;
- an atmospheric relative humidity (e.g., ~0%, arid, ~100%, raining);
- an atmospheric pressure;
- a measure of atmospheric pollution, such as ionization, particulates, or amount of $SO_2$ or other pollutant;
- a measure of atmospheric allergens;
- other indicators of dry eyes effects.

For example, as further described herein, the digital eyewear 100 can consider a light intensity, whether a total light intensity or a light intensity for a selected frequency range (such as ultraviolet light, blue light, or any other frequencies to which the patient 180 might be susceptible). When the light intensity, whether total or in a selected frequency range, is sufficient to affect the patient's (180) eye, the digital eyewear 100 can consider that information when determining the likelihood of a near-term or current dry eyes effect. As further described herein, the digital eyewear 100 can also provide an adjusted sensory input 122 by modifying the external sensory input 121, such as by shading/inverse-shading the external sensory input 121 to remove excess luminosity.

For another example, with respect to weather conditions such as atmospheric humidity or atmospheric pressure, the digital eyewear 100 can consider that information when determining the likelihood of a near-term or current dry eyes effect. When the atmospheric humidity is relatively low (that is, local conditions are relatively arid), the likelihood of a near-term or current dry eyes effect might be increased. When the atmospheric pressure is changing rapidly, this might indicate the possibility of precipitation, with the effect that the likelihood of a near-term or current dry eyes effect might be decreased. When the local temperature is relatively low and the atmospheric humidity is relatively low (that is, cold and dry conditions), the likelihood of a near-term or current dry eyes effect might be increased.

For another example, with respect to atmospheric pollution, such as ionization (possibly due to ozone, $O_3$), particulates (possibly due to unburned hydrocarbons), or other pollutants, the patient's (180) eye might be affected, and the likelihood of a near-term or current dry eyes effect might be increased. The digital eyewear 100 can consider that information when determining the likelihood of a near-term or current dry eyes effect.

For another example, with respect to atmospheric allergens, the digital eyewear 100 can determine a physical location of the patient, such as using a GPS device (not shown), and can access a data repository 191 to obtain a report of allergens currently active at that time and place. Allergens such as pollen might have many different types of pollen count; the inventor understands there are at least 12 such types. Alternatively, the ambient sensors 140 can include a pollen detector, or one such pollen detector for each significant type of pollen to which the patient 180 might be susceptible.

In one embodiment, similar to the method described in the Incorporated Disclosures, the digital eyewear 100 can determine a current dry eyes effect, and a measure of its severity. For example, the digital eyewear 100 can determine a measure of pain, or a measure of likelihood that the dry eyes effect will further develop into a more debilitating event, or a measure of likelihood that the dry eyes effect is indicative of a more serious medical trauma (such as ocular ulcer or an eye infection).

At a step 422, similar to the method described in the Incorporated Disclosures, the digital eyewear 100 maintains a record of the dry eyes effect, and reports that record to one or more data repositories 191.

The method proceeds with the next flow point.

Prediction of Dry Eyes Effects

At a flow point 430, similar to the method described in the Incorporated Disclosures, the digital eyewear 100 is ready to predict dry eyes events.

At a step 431, similar to the method described in the Incorporated Disclosures, the digital eyewear 100 accesses a record of dry eyes events, from one or more data repositories 191 and from the memory of its computing device 161.

At a step 432, similar to the method described in the Incorporated Disclosures, the digital eyewear 100 assigns a set of weights to each sensor value it receives, such as from the patient sensors 130 and the ambient sensors 140. For example, similar to the Incorporated Disclosures, the digital eyewear 100 can assign one weighting value (or a time-varying function from which it can determine a weighting value) to each such time series of such sensor values. For example, the digital eyewear 100 can receive the set of weights, or the set of functions from which time varying weights are determined, from one or more data repositories 191.

At a step 433, similar to the method described in the Incorporated Disclosures, the digital eyewear 100 conducts an "adaptive tuning" (or "self-tuning") technique to adjust the weights it has assigned to each sensor value (or the time varying weights it has assigned to each time varying sensor value). For example, the digital eyewear 100 can use an adaptive control technique to minimize error between the weighted determination of results (in response to sensor inputs) and the actual results (in response to actual measurement). In such cases, the digital eyewear 100 can be responsive to actual determination of dry eyes events to adjust its parameters for future prediction of digital eyewear 100 from input sensors. In one embodiment, the digital eyewear 100 can determine its prediction of likelihood of future dry eyes events in response to input sensors using a linear weighted model, similar to the Incorporated Disclosures.

While this Application primarily describes use of adaptive tuning, in the context of the invention, there is no particular requirement for any such limitation. Any time series adjustment technique would be suitable, and could be used in the context described.

This Application describes methods by which the digital eyewear 100 can predict dry eyes effects. Similar to the method described in the Incorporated Disclosures, the digital eyewear 100 can determine, in a similar manner, whether the patient 180 actually has a current dry eyes effect, whether a particular treatment will ameliorate the patient's dry eyes effect, whether the dry eyes effect will recur, whether a particular patient 180 will respond to a suggested method of patient self-care, and whether a particular patient 180 will respond to a particular method of reinforcing successful patient self-care (above and beyond the patient 180 having been reinforced by actual success of the self-care by avoidance or treatment of a dry eyes effect).

At a step 434, similar to the method described in the Incorporated Disclosures, the eyewear controller 160 can report its adjusted weights to one or more data repositories 191. In one embodiment, the eyewear controller 160 can report its adjusted weights if they differ substantially from the original weights the eyewear controller 160 received. As part of this step, the receiving data repositories 191 adjust their stored weights in response to the adjustments reported by the eyewear controller 160. In one embodiment, the receiving data repositories 191 maintain their stored weights in response to multiple digital eyewear 100 devices; thus, they adjust their stored weights only when adjustments reported by individual eyewear controllers 160 are correlated and indicate that their stored weights were not thoroughly accurate.

The method proceeds with the next flow point.

Prevention of Dry Eyes Effects

At a flow point 440, similar to the method described in the Incorporated Disclosures, the digital eyewear 100 is ready to prevent future dry eyes effects.

At a step 441, similar to the method described in the Incorporated Disclosures, the digital eyewear 100 receives time-varying information from the patient sensors 130 and the ambient sensors 140.

At a step 442, similar to the method described in the Incorporated Disclosures, the eyewear controller 160 predicts whether a dry eyes effect is about to occur near term.

At a step 443, similar to the method described in the Incorporated Disclosures, the eyewear controller 160 directs the digital eyewear 100, such as the lenses 120, to provide an adjusted sensory input 122 with a reduced likelihood of a near-term dry eyes effect.

In one embodiment, as described herein, similar to the method described in the Incorporated Disclosures, the digital eyewear 100 can be responsive to visual triggers of a dry eyes effect, such as by canceling those visual triggers in the adjusted sensory input 122. For example, the digital eyewear 100 can cancel those visual triggers by shading/inverse-shading of those visual triggers.

In such cases, similar to the method described in the Incorporated Disclosures, shading/inverse-shading can be performed by one or more of the following:

LCD elements in the lenses 120, electrically controlled between clear and opaque states;

for selected frequencies, by antireflective coatings in the lenses 120, or by electrically controlled adaptive anti-reflective coatings therein;

for selected frequencies, by electrically controlled e-chromatic elements embedded in the lenses 120;

for selected frequencies, by electrically controlled micro-mechanical elements (such as MEMS) embedded in the lenses 120;

for selected frequencies, by electrically controlled elements constructed from one or more of: grapheme (or other allotropes of carbon, such as carbon nanotubes or fullerenes), astrophotonics, nanomaterials, electro-nanomaterials, electrophotonics, electropolymers, or other materials;

other aspects of shading/inverse-shading as further described in the Incorporated Disclosures.

In one embodiment, similar to the method described in the Incorporated Disclosures, prevention of dry eyes effects can be particularized to individual patients 170. For example, each patient 180 might have an individual response to blink rate, light, or other senses. For another example, each patient 180 might have an individual response to their sleep cycle, and thus might have a differential response to time of day and day of the week. For another example, each patient 180 might have an individual response to the ambient environment, as some patients 170 might be more sensitive to weather, to pollutants, or to allergens (and when sensitive to allergens, to different allergens). For another example, each patient 180 might have an individual response to medication, such as prescription medication (e.g., sedatives) or non-prescription medication (e.g., antihistamines).

The method proceeds with the next flow point.

Treatment of Dry Eyes Effects

At a flow point 450, similar to the method described in the Incorporated Disclosures, the digital eyewear 100 is ready to treat current dry eyes effects.

At a step 451, similar to the method described in the Incorporated Disclosures, the digital eyewear 100 treats current dry eyes effects similarly to preventing future dry eyes effects, with the primary difference being that the eyewear controller 160 can be responsive to the patient's actual dry eyes effect, rather to a prediction thereof. For example, the digital eyewear 100 can be disposed to reduce the length or severity of the current dry eyes effect, or to reduce the likelihood of the current dry eyes effect increasing in severity. In such cases, whether the digital eyewear 100 prefers to reduce the length of the current dry eyes effect, or to reduce its severity, or to reduce the likelihood of an increase in severity, can be responsive to the patient 180, or can be responsive to medical parameters received from data repositories 191, or can be responsive to medical personnel.

For another example, similar to the method described in the Incorporated Disclosures, the digital eyewear 100 can be disposed to cause its communicators 162 to exchange messages with one or more data repositories 191, or medical personnel, with respect to the current dry eyes effect.

Training Self-Care

At a flow point 460, similar to the method described in the Incorporated Disclosures, the digital eyewear 100 is ready to train patients to improve their self-care.

As further described herein, the patient can engage in actions to reduce the likelihood of a dry eyes effect. The digital eyewear 100 can alert the patient when the likelihood of a dry eyes effect exceeds an acceptable threshold, and can suggest that the patient 180 take action to alleviate the problem. When the patient 180 does take the suggested action, or any other action with substantial self-care effect, the digital eyewear 100 can provide the patient 180 with positive feedback, hopefully reinforcing patient efforts at self-care.

At a step 461, similar to the method described in the Incorporated Disclosures, the digital eyewear 100 receives time-varying information from the patient sensors 130 and the ambient sensors 140.

At a step 462, similar to the method described in the Incorporated Disclosures, the eyewear controller 160 predicts whether a beginning of a dry eyes effect is about to occur near term.

At a step 463, similar to the method described in the Incorporated Disclosures, the eyewear controller 160 directs the digital eyewear 100, such as the lenses 120, to provide an adjusted sensory input 122 that alerts the patient 180 with respect to the likelihood of a beginning of a dry eyes effect, and that suggests efforts at self-care.

At a step 464, similar to the method described in the Incorporated Disclosures, the eyewear controller 160 receives information from the patient sensors 130 indicative of whether the patient 180 has made efforts at self-care.

In one embodiment, similar to the method described in the Incorporated Disclosures, the eyewear controller 160 can determine whether the likelihood of a beginning of a dry eyes effect has been reduced, and can deem that the patient 180 has made efforts at self-care whenever this is so.

In one embodiment, similar to the method described in the Incorporated Disclosures, the eyewear controller 160 can provide an adjusted sensory input 122 that that asks the patient 180 whether they have engaged in the suggested self-care, and can deem that the patient 180 has done so whenever the patient 180 answers affirmatively.

In one embodiment, similar to the method described in the Incorporated Disclosures, the eyewear controller 160 can determine, in response to the patient sensors 130 and the ambient sensors 140, whether the patient 180 has engaged in the suggested self-care. For example, if the digital eyewear 100 has suggested that the patient 180 refocus on a more distant object, the eyewear controller 160 can examine the patient sensors 130 to determine if the patient's eyes are in fact so re-focused. In such cases, the eyewear controller 160 can determine whether the patient 180 has engaged in the suggested self-care.

At a step 465, similar to the method described in the Incorporated Disclosures, when the eyewear controller 160 deems that the patient 180 has engaged in the suggested self-care, the digital eyewear 100 can reinforce the patient's action.

In one embodiment, similar to the method described in the Incorporated Disclosures, the eyewear controller 160 can provide an adjusted sensory input 122 that that congratulates the patient 180 for engaging in the suggested self-care. For example, the eyewear controller 160 can present a message to the patient 180 saying so. For another example, the eyewear controller 160 can gamify the self-care by awarding the patient 180 a selected number of "experience points" for engaging in the suggested self-care. In such cases, medical personnel can optionally reward the patient 180 with extra attention (such as a congratulatory phone call), with gift cards (for example, insurance companies might find it less expensive to give out a free Big Mac™ than to pay for another doctor visit), with one or more stickers, or with some other positive reinforcement.

The method continues with the next flow point.

End of Method

A flow point 400B indicates that the method 400 is ready to finish. The method 400 finishes operations and cleans up after any ongoing operations. For example, when using an electronic controller, the controlling device de-allocates and possibly erases any terminated storage values. The method 400 performs any terminating routines, and where applicable, transfers power control to a sleep mode or a shutdown mode.

The method 400 can be restarted as triggered by any technique described with respect to the flow point 400A.

Example Communication Systems

FIG. 5 shows a conceptual drawing of an example communication system.

A system 500 can include elements as shown in the figure, and as otherwise described herein, such as:
  the digital eyewear 100;
  the eyewear controller 160, including its computing device 161 and one or more communicators 162 and their sending/receiving elements;
  one or more communication links 210;
  one or more data repositories 191;
  one or more communicators with respect to medical personnel 192;
  other elements as further described in the Incorporated Disclosures.

The eyewear controller 160 for the digital eyewear 100 can be coupled, under control of its computing device 161 and using its communicators 162, to the communication links 210. The communication links 210 can be coupled to a communication network such as the internet, by which they can access one or more of the data repositories 191.

As described herein, the digital eyewear 100 can perform its operations in response to a collective database, such as a collective database that is remotely maintained and is updated with respect to patient information with respect to dry eyes. For example, each instance of digital eyewear 100, that is, digital eyewear 100 for each patient, can report its information to the data repositories 191, with the effect that the data repositories 191 can maintain collective data with respect to patients and any dry eyes effects.

Collective data can also include information injected into data repositories 191 by known data sources, such as weather reports, pollution control reports, and allergen reports. For example, known data sources can associate information with respect to weather (e.g., current and predicted weather conditions), pollution (e.g., current and predicted air pollution levels), and allergens (e.g., current and predicted pollen counts), and can deliver that information to digital eyewear 100 in response to GPS location information. This can have the effect that each instance of digital eyewear 100 does not need to independently measure weather, pollution, or allergens, and does not need to attempt to predict future conditions thereof.

As described herein, the digital eyewear 100 can also perform its operations in coordination with other instances of digital eyewear 100, such as for example coordinating action to ameliorate or treat dry eyes effects in response to nearby patients 170. For example, when a first instance of digital eyewear 100 reports a substantial disturbance (such as a substantial change in allergens, air pressure, humidity, or pollution) that might have a dry eyes effect on a patient 180 using a second instance of digital eyewear 100, the first digital eyewear 100 can inform the second digital eyewear 100 thereof. The first digital eyewear 100 can communicate with the second digital eyewear 100 under control of their computing devices 161 and using their communicators 162.

For another example, when a first patient 180 using a first instance of digital eyewear 100 and a second patient 180 using a second instance of digital eyewear 100 are participating in a joint activity (such as both playing a video game on a digital computer), the first instance of digital eyewear 100 can inform the second instance of digital eyewear 100 of any changes in conditions that affect the first patient 180 and that might affect the second patient 180. In such cases, the first instance of digital eyewear 100 can also inform the second instance of digital eyewear 100 of any alterations to light effects (such as shading any sudden brightness from the video game) that the first instance of digital eyewear 100 decided to apply. The second instance of digital eyewear 100 can choose to apply similar alterations to light effects.

Alternatively, when the first patient 180 and the second patient 180 are not similarly situated, such as when the first patient 180 and the second patient 180 have differing reactivity to light regarding dry eyes effects, the first instance of digital eyewear 100 and the second instance of digital eyewear 100 can determine to take differing steps in response to changes in the light environment. For example, when the first patient 180 is more sensitive than the second patient 180 to dry eyes effects, the first instance of digital eyewear 100 can take more aggressive action than the second instance of digital eyewear 100, to reduce the likelihood or severity/duration of dry eyes effects.

Example Medical Examination Systems

Figure 6A:
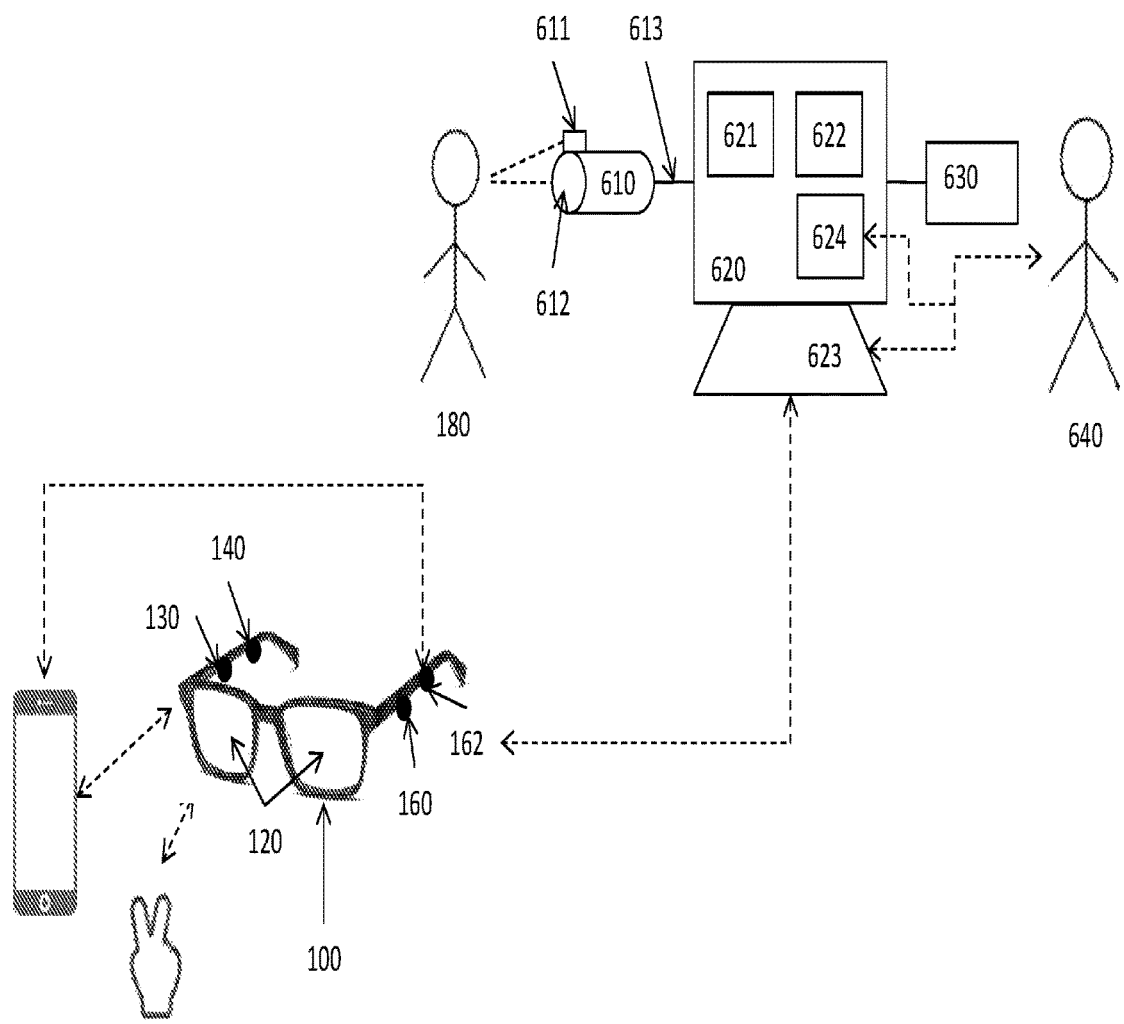
FIG. 6A shows a conceptual drawing of an example system for using digital eyewear in combination with medical examination.
Figure 6B:
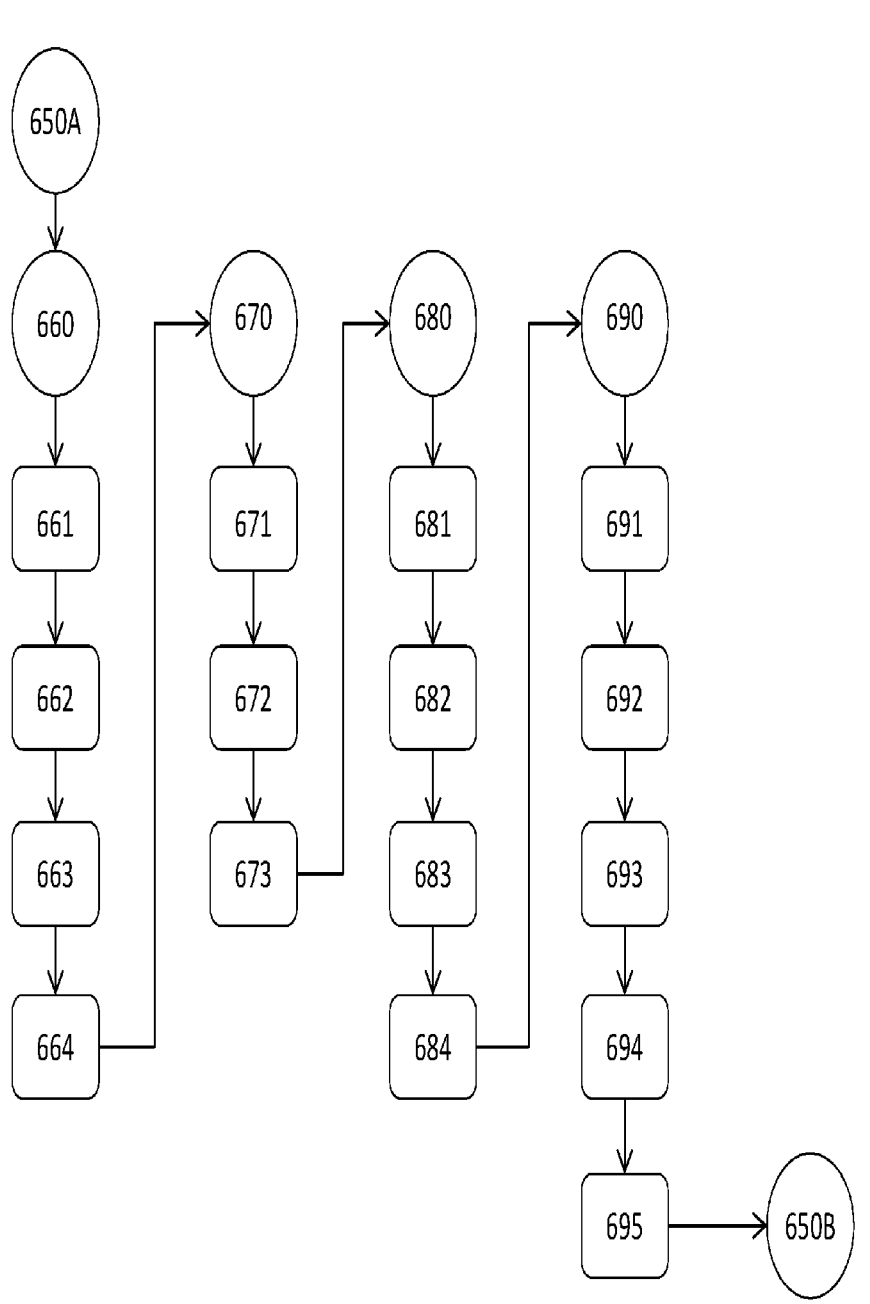
FIG. 6B shows a conceptual drawing of an example method of using digital eyewear in combination with medical examination.

FIG. 6A shows a conceptual drawing of an example system for using digital eyewear in combination with medical examination. FIG. 6B shows a conceptual drawing of an example method of using digital eyewear in combination with medical examination.

Example Systems

FIG. 6A shows a conceptual drawing of an example system for using digital eyewear in combination with medical examination. A system 600 can include elements as shown in the figure, and as otherwise described herein, such as:
the digital eyewear 100;
a patient eye sensor 610;
a medical computing device 620;
a patient eye display 630; and
one or more medical personnel 640 (not part of the system 600).

For example, the patient eye sensor 610, medical computing device 620, and patient eye display 630, can be disposed as part of, coupled to, or otherwise operating with, one or more eye examination devices, such as the Oculus Keratograph 5M™, http://www.oculus.de/us/landingpages/k5m-dryeye/ (enclosed as a Technical Appendix to this Application, hereby incorporated by reference), or a similar device, or a device performing similar functions. The eye examination devices can be disposed to measure or otherwise determine features with respect to dry eyes, such as: bulbar and limbal redness of the eye, such as in response to blood vessels in the conjunctiva of the eye; tear film features, such as tear film break-up time, meniscus tear height, and otherwise; Meibography measures; lipid layer depth, such as using lipid layer interferometry; tear film viscosity and other tear film dynamics, such as determined using videography of the eye; other tear film features; and otherwise.

In one embodiment, the patient eye sensor 610 and medical computing device 620 can measure redness of the eye with respect to an amount of redness showing on the conjunctiva of the patient's (180) eye, and otherwise in response to blood vessels apparent on the surface of the patient's (180) eye.

In one embodiment, the tear film break-up time (sometimes referred to as "TBUT", or with respect to the "Oculus Keratograph 5M"™, as "NIKBUT") can include a measure of duration between a time when the patient 180 blinks and when a dry spot appears on the patient's (180) eye.

In one embodiment, the meniscus tear height can include a measure of thickness of the aqueous layer 312 of the patient's (180) tear film 310.

In one embodiment, the Meibography measures can include one or more measures with respect to the Meibomain glands 321 of the patient's (180) eye.

In one embodiment, the lipid layer depth can include a measure of thickness of the lipid layer 311 of the patient's (180) tear film 310.

In one embodiment, the tear film viscosity can include a measure responsive to a time during which the patient's (180) tear continues to lubricate the patient's (180) eye.

In one embodiment, the medical personnel 640 can also assess possible dry eyes conditions in response to examination of one or more of the following:
inflammation of the patient's (180) eye, or a portion thereof;
one or more measures of blood oxygenation, such as a blood oxygenation measure, a breathing rate, or a pulse rate, particularly when applicable to blood vessels in or near the patient's (180) eye;
operation of the patient's (180) eyelids, such as whether the patient's (180) eyelids close completely or only partially when the patient 180 blinks;
presence of allergies or irritants in or around the patient's (180) eye;
presence of bacteria or bacteriological effects (such as bacteriological effluvia) in or around the patient's (180) eye;
presence of dirt, infection (such as a sty), pus, "scurf," or other occlusions or stoppages in or around the patient's (180) eye;
symptoms of sleep apnea, patient's (180) complaints with respect to conditions that are associated with sleep apnea;

tear film debris;
tear film dynamics with respect to formation, break-up and disappearance; and
any other environmental or systemic effects with respect to the patient's (180) eyes.

For example, the patient eye sensor 610, medical computing device 620, and patient eye display 630 (such as embodied in the Oculus Keratograph 5M™) can be examined by medical personnel 640 using florescence imaging. In such cases, the florescence imaging can include still photography, video photography, other imaging usable by medical personnel 640, and otherwise.

In one embodiment, the medical personnel 640 can also assess possible dry eyes conditions in response to one or more patient self-reports. For example, the medical personnel 640 can ask the patient 180 to verbalize when the patient 180 is feeling dryness, itching, scratchiness, or other possible dry eyes effects. For another example, the patient 180 can indicate the presence (or absence, despite information from the patient eye sensor 610) of one or more dry eyes effects by presenting a selected hand or body gesture for detection by the digital eyewear 100, by presenting a selected eye gesture to the digital eyewear 100, by manipulating a smartphone or other mobile device, or some other patient input, or a combination of more than one such input.

In such cases, the hand or body gesture can be presented by bringing a portion of the patient's hand or body to within a field of view of the digital eyewear 100, possibly in combination with directing the patient's gaze at the hand or body gesture. For example, the digital eyewear 100, such as the control element 160 thereof, can detect the hand or body gesture in response to object recognition of the patient's hand or body. For another example, the digital eyewear 100, such as the control element 160 thereof, can be trained using a machine learning technique to determine the presence of the hand or body gesture, and can thereafter detect it in response to a (still or video) image of the hand or body gesture as presented in the field of view of the digital eyewear 100.

In such cases, the smartphone or other mobile device can operate under control of a mobile app, such as a program disposed for receiving patient input and communicating that patient input to the medical personnel 640. For example, the smartphone or other mobile device can communicate with the medical computing device 620, such as using one or more input elements thereof (as those input elements are further described herein). Alternatively, the smartphone or other mobile device can communicate directly with the medical personnel 640, such as by communicating with the medical personnel's own smartphone or other mobile device.

In such cases, the eye gesture can include one or more of: an eye blink, a glance right/left or up/down, an eye blink combined with a glance, a selected eye gesture combined with another patient input, or otherwise. For example, the digital eyewear 100 can detect the eye gesture in response to gaze tracking of the patient's (180) eyes, using its one or more gaze tracking elements.

For another example, the medical personnel 640 can determine whether the patient's (180) dry eye condition is associated with other medical conditions possibly related to the eyes, such as migraines (which can be triggered or aggravated by excessive light or glare), photophobia, other sensitivity to light or particular frequencies thereof, and otherwise.

Patient Eye Sensor

The patient eye sensor 610 can include elements as shown in the figure, and as otherwise described herein, such as:
one or more illumination elements 611;
one or more cameras 612; and
one or more communication links 613 coupled to the medical computing device 620.

The patient eye sensor 610 can be disposed to examine the patient's (180) eye, or both of them, with respect to features related to dry eye conditions and related medical issues. As further described herein, the patient eye sensor 610 can be disposed to measure or otherwise determine medical parameters with respect to the patient's (180) eye, such as tear film features described above; other tear production, adhesion, break-up, or evaporation features; other medical features of the patient's (180) eye; or otherwise.

The illumination elements 611 can be directed at the patient's (180) eye, or both of them, or more specifically at elements of the patient's (180) eye relating to dry eyes conditions. The illumination elements 611 can be disposed to emit white light (such as to measure redness of the eye, tear film break-up time, tear viscosity, and possibly other features), blue light at 465 nm, infrared at 840 nm or 880 nm, or other selected electromagnetic frequencies.

The cameras 612 can be responsive to light reflected or refracted by the patient's (180) eye in response to the illumination elements 611. For example, the cameras 612 can include a digital CCD camera having approximately 22,000 data points disposed across its field of imaging.

For another example, the cameras 612 can include an interferometer disposed to measure or otherwise determine one or more electromagnetic frequencies relatively strongly returned from the tear film, or one of its layers, in response to electromagnetic frequencies directed by the illumination elements 611 at the patient's (180) eye. Measured, or otherwise determined, electromagnetic frequencies relatively strongly returned from the tear film, or one of its layers, can be used by the medical computing device 620 to noninvasively determine a depth of the tear film, or one of its layers.

The communication link 613 can be coupled to the illumination elements 611, the cameras 612, and the medical computing device 620. The medical computing device 620 can use the communication link 613 to control the illumination elements 611 and the cameras 612, and to receive and maintain data from the cameras 612.

Patient Eye Display

The patient eye display 630 can include elements as shown in the figure, and as otherwise described herein, such as: a computing display disposed to present still or moving images to medical personnel 640, in response to information from the patient eye sensor 610, and in response to controls from medical personnel 640.

For example, as further described herein, the patient eye display 630 can present one or more still or moving images of the patient's (180) eyes in response to white light, or in response to one or more selected frequencies of light. Medical personnel 640 can review the images of the patient's (180) eyes, such as to determine whether the patient's (180) eyes have excessive redness, inadequate tear break-up time (such as under 10 seconds), inadequate tear meniscus height, damage or degradation of the Meibomian glands, inadequate lipid layer thickness, untoward tear film viscosity, other dry eyes or related conditions, or otherwise.

Medical Computing Device

The medical computing device 620 can include elements as shown in the figure, and as otherwise described herein, such as:

a processor or other computing element 621;

a computer memory 622;

one or more input elements 623; and one or more output elements 624.

The medical computing device 620 can receive information from the patient eye sensor 610 and present information to the patient eye display 630. This can have the effect that medical personnel 640 can determine a status of the patient's (180) eyes, including: whether a dry eye condition exists, its severity, and progress of any damage to the patient's (180) eyes. This can have the effect that medical personnel 640 can perform an examination of the patient's (180) eyes, evaluating their status and prescribing treatment as might be necessary or desirable.

The medical computing device 620 can also receive information from medical personnel 640 with respect to examination of the patient's (180) eyes, including medical personnel's (640) assessments of the status of the patient's (180) eyes. This information can include whether a dry eyes condition exists, its severity, and any possible damage to the patient's (180) eyes. This can have the effect that each set of information collected by the medical computing device 620 with respect to the examination can be tagged with the medical personnel's (640) assessments of the status of the patient's (180) eyes.

Machine Learning Techniques

The medical computing device 620 can perform a machine learning technique with respect to the information it receives from the patient eye sensor 610, in response to the tagged assessments by medical personnel 640 of that information. For example, the medical computing device 620 can perform one or more of the following machine learning techniques.

In one embodiment, the medical computing device 620 can determine a set of weights in an artificial neural network, such as a "deep learning" artificial neural network. The inputs to the neural network can include the information the medical computing device 620 receives from the patient eye sensor 610. The medical computing device 620 can tag each received set of information in response to the assessments of that information by medical personnel 640. This can have the effect that the medical computing device 620 can train the neural network in response to a tagged set of inputs. In such cases, the inputs can include the information the medical computing device 620 receives from the patient eye sensor 610; the outputs can include the tags provided by medical personnel 640. The neural network is trained so that its outputs adequately match the tags provided by medical personnel 640.

Real-Time Determination of Dry Eyes Conditions

In such cases, this can have the effect that the medical computing device 620, using the neural network, can receive inputs similar to the information received from the patient eye sensor 610. The medical computing device 620 can send the weights associated with the neural network to the digital eyewear 100, whose eyewear controller 160 can thus perform the same or similar operations as the medical computing device 620. The eyewear controller 160 can (A) receive information from one or more of the lenses 120, the patient sensors 130, or the ambient sensors 140; (B) provide that information to the eyewear controller 160 to perform the same or similar operations as the neural network; and (C) determine whether the information from the lenses 120, the patient sensors 130, or the ambient sensors 140, indicates the presence of a dry eyes condition. This can have the effect that a relatively low-resolution camera can be used by the digital eyewear 100 to detect medical conditions that might otherwise involve a relatively high-resolution camera used by the medical personnel 640. This can also have the effect that the digital eyewear 100 can use a relatively low-resolution camera, in addition to or in lieu of assistance by medical personnel 640, to determine the likelihood, presence, or severity of a dry eyes condition.

Inputs from the relatively low-resolution camera used by the digital eyewear 100 can be used in addition to the relatively high-resolution camera used by the patient eye sensor 610, to provide at least some of the inputs to the machine learning techniques. Inputs from patient evaluations of whether the patient feels a dry eyes condition can also be used in addition to inputs from medical personnel 640 evaluations of whether the patient has a dry eyes condition. For example, as to some dry eyes conditions, the patient might more easily detect them; while as to other dry eyes conditions, the medical personnel 640 might more easily detect them.

In addition to determining the likelihood, presence, or severity of a dry eyes condition, the eyewear controller 160 can also record the conditions associated with the dry eyes condition, and record and maintain that information in a memory of its computing device 161, or in a memory of a device accessible using its communicator 162, or using another information storage technique, or otherwise. When the digital eyewear 100 next communicates with the medical computing device 620, such as using its communicator 162, or when the digital eyewear 100 is next brought to the medical personnel 640, or otherwise, the information associated with the dry eyes condition can be sent to the medical computing device 620, presented by its associated patient eye display 630, and reviewed by medical personnel 640. This can have the effect that medical personnel 640 can make a detailed review of dry eyes conditions that occur to the patient 180 from time to time, without any particular requirement that the patient 180 spend a relatively lengthy time at the medical personnel's (640) office, or that the medical personnel 640 spend a relatively lengthy time with the patient 180, waiting for the dry eyes condition to occur.

With the information provided by the medical computing device 620 and the medical personnel 640, the eyewear controller 160 can more accurately and more reliably determine the likelihood, presence, or severity of a dry eyes condition. As further described herein, when the eyewear controller 160 determines the presence of a dry eyes condition (with greater than a selected likelihood, or greater than a selected severity when the dry eyes condition is considered likely), the eyewear controller 160 can trigger one or more of the treatment devices 150. Better accuracy and reliability allows the digital eyewear 100 to be more aggressive (when necessary) about when to trigger the treatment devices 150, and when they are triggered, more accurate and reliable what degree of treatment is desirable.

While this Application primarily describes use of a deep learning neural network when determining when a dry eyes condition occurs (and the likelihood, presence, or severity thereof), in the context of the invention, there is no particular requirement for any such limitation. Any other artificial intelligence (AI) or machine learning (ML) technique would be suitable, and could be used in the context described. For example, the control element 160 could use a Kohonen Network or a Random Forest technique to separate the information with respect to the possible contexts in which dry eyes conditions might occur into a set of clusters, each with its own associated information. See (Wikipedia, "Machine Learning") and references cited therein, and (Wikipedia, "Artificial Intelligence") and references cited therein, each of which is hereby incorporated by reference.

The digital eyewear 100 can also receive information from medical personnel 640 with respect to a diagnosis or treatment of dry eyes conditions for the patient 180, including information for determining whether a dry eye condition exists, its severity, and a best manner of treatment thereof. In operation other than in the presence of medical personnel 640, the digital eyewear 100 (such as its control element 160) can use the information from medical personnel 640 in combination or conjunction with information from the lenses 120, the patient sensors 130, or the ambient sensors 140, to determine whether a dry eye condition exists, its severity, a best manner of treatment thereof, and a likelihood of patient self-care if the patient is alerted to do so.

Example Methods of Operation

FIG. 6B shows a conceptual drawing of an example method for using digital eyewear in combination with medical examination.

As further described herein, methods of operation can include steps as described herein. While the steps are shown and described in a linear order, in the context of the invention, there is no particular requirement for any such limitation. Except where explicitly stated, there is no particular requirement for the steps to be encountered or performed linearly, or in any particular order or by any particular device. For example and without limitation, the steps can be encountered or performed in parallel, in a pipelined manner.

As further described herein, one or more portions of the methods are sometimes described as being performed by particular elements of the systems described herein, or sometimes by the method itself. When a flow point or method step is described as being performed by the method, it can be performed by one or more of those elements, by one or more portions of those elements, by an element not described with respect to the figure, by a combination or conjunction thereof, or otherwise.

A method 650 includes flow points and method steps as shown in the figure, and as otherwise described herein, such as:

a flow point 650A, at which the method 650 is ready to begin;

a flow point 660, at which the method 650 is ready to initiate parameters for the digital eyewear;

a flow point 670, at which the digital eyewear 100 is ready to conduct real-time determination of dry eyes conditions;

a flow point 680, at which the digital eyewear 100 is ready to respond to its realtime determination of dry eyes conditions;

a flow point 690, at which the digital eyewear 100 is ready to report information about its real-time determination of dry eyes conditions;

a flow point 650B, at which the method 650 is ready to finish.

Beginning of Method

A flow point 650A indicates that the method 650 is ready to begin.

The method 650 can be triggered by one or more of the following:

an input (or other signal from an input/output device 170 or one of the input elements 623) requesting that the method 650 is started, or an input or other signal from the medical computing device 620;

the digital eyewear 100 detecting that it is present at an office of medical personnel 640, such as in response to a location device, or in response to an input to the lenses 120 (that is, the digital eyewear 100 can perform object recognition on the medical);

a message from an external device 190 or from medical personnel 192;

an alert or signal from one or more of the patient sensors 130 or ambient sensors 140;

or as otherwise described herein.

The method 650 proceeds with the next flow point.

Initiate Parameters

A flow point 660 indicates that the method 650 is ready to initiate parameters for the digital eyewear 100.

At a step 661, the patient 180 can wear the digital eyewear 100 while the medical personnel 640 can use one or more of: the patient eye sensor 610, the medical computing device 620, or the patient eye display 630. The medical personnel 640 can couple the patient eye sensor 610 to the patient's (180) eye, and can review possible dry eyes conditions that the patient 180 might be undergoing. The medical personnel 640 can indicate to the medical computing device 620, such as by using the one or more input elements 623, the presence/likelihood or severity of any dry eyes conditions. For example, the medical personnel 640 can indicate the presence/likelihood or severity of both current and future dry eyes conditions (such as the likelihood of presence of current dry eyes conditions, the likelihood of development of future dry eyes conditions, or the severity of either or both).

As part of this step, the medical personnel 640 can indicate other and further information, such as one or more of the following:

an expected range of time at which a future dry eyes condition is expected to develop;

an expected duration during which a current or future dry eyes condition is expected to last;

an expected likelihood of damage to the patient's (180) eye due to a current or future dry eyes condition;

a likelihood of successful treatment of a current or future dry eyes condition, a degree of amelioration in response to treatment of a current or future dry eyes condition, or other information with respect to treatment;

a likelihood of whether the patient 180 will respond to a prompt to conduct self-care with respect to a current or future dry eyes condition; a likelihood of whether the patient's (180) response will be successful (and to what degree) in treating a current or future dry eyes condition; or a likelihood or whether the patient's (180) self-care response will be reinforced by a selected reward; or any other assessments by or information from the medical personnel 640.

At a step 662, the medical computing device 620 can receive information with respect to the patient's (180) eyes, and can receive information with respect to assessments by the medical personnel 640 of possible dry eyes conditions. As part of this step, the medical computing device 620 can receive information from the digital eyewear 100, such as information from one or more of: light incoming to the lenses 120, the patient sensors 130, the ambient sensors 140, one or more patient inputs (such as from an input device or a hand gesture or eye gesture by the patient 180), any other information available to the digital eyewear 100, or otherwise.

At a step 663, the medical computing device 620 can train an artificial neural network, such as a deep learning neural network, with neural connection weights. This can have the effect that the artificial neural network provides a relatively high accuracy assessment of whether the patient is undergoing a dry eyes condition. In such cases, the medical computing device 620 can continue to train the artificial neural network until the desired accuracy is obtained. For example, a relatively high accuracy can include a 90% rate that the assessment is true (that is, neither a false positive nor a false negative).

As part of this step, the medical computing device 620 can offload some of its training effort, such as by off-loading some of its work to a logically remote device for training the artificial neural network, by requesting the assistance of the digital eyewear 100 for training the artificial neural network, or otherwise.

Also as part of this step, the medical computing device 620 (with or without assistance from one or more other devices) can generate one or more hypothetical sets of information with respect to the patient's (180) eyes, and can ask the medical personnel 640 to provide an assessment of whether those hypothetical sets of information indicate a dry eyes condition. For example, when the medical computing device 620 has difficulty determining whether selected information indicate dry eyes conditions, the medical computing device 620 can generate information that is similar and ask the medical personnel 640 to evaluate that similar information. This can have the effect that the medical computing device 620 can effectively ask the medical personnel how important selected features of the information are when determining whether the patient 180 is undergoing one or more dry eyes conditions.

At a step 664, the medical computing device 620 can send the training information with respect to the artificial neural network to the digital eyewear 100 (such as the eyewear controller 160 at the digital eyewear 100). The digital eyewear 100 can receive the training information and maintain that training information for use by its eyewear controller 160. The eyewear controller 160 can use that training information to perform assessments of dry eyes conditions using a similar artificial neural network, such as using its own processor and memory.

The method 650 proceeds with the next flow point.

Real-Time Determination of Dry Eyes Conditions

A flow point 670 indicates that the method 650 is ready to conduct real-time determination of dry eyes conditions.

At a step 671, the digital eyewear 100 can receive information from one or more of: light incoming to the lenses 120, the patient sensors 130, the ambient sensors 140, one or more patient inputs (such as from an input device or a hand gesture or eye gesture by the patient 180), or any other information available to the digital eyewear 100. For example, as part of this step, inputs available to the digital eyewear 100 can provide feature information to the artificial neural network.

At a step 672, the digital eyewear 100 (such as the eyewear controller 160 at the digital eyewear 100) can use the training information to perform assessments of dry eyes conditions using a similar artificial neural network, such as using its own processor and memory. For example, as part of this step, the eyewear controller 160 can apply the neural network weights to the feature information that was input at the previous step.

As part of this step, the information available to the digital eyewear 100 is generally from one or more relatively low-resolution cameras, such as might be coupled to the lenses 120 or the ambient sensors 140. This is often in contrast to relatively high-resolution cameras available to medical personnel 640 using the patient eye sensor 610 or equipment coupled thereto. This can have the effect that the artificial neural network can be more sensitive to feature information than would ordinarily be achievable by training using the low-resolution cameras otherwise available to the digital eyewear 100.

At a step 673, the digital eyewear 100 can provide one or more assessments of current or future dry eyes conditions, such as presence/likelihood and severity, duration, treatment and amelioration, and patient prompting/reinforcement of self-care. For example, the eyewear controller 160 can provide one or more outputs of the artificial neural network.

The method 650 proceeds with the next flow point.

Responding to Real-Time Determine of Dry Eyes Conditions

A flow point 680 indicates that the method 650 is ready to perform actions in response to its real-time determination of dry eyes conditions.

At a step 681, the digital eyewear 100 can use its assessments to perform operations in response to the presence/likelihood or severity of current or future dry eyes conditions.

At a step 682, the eyewear controller 160 can, responsive to the presence/likelihood or severity of current or future dry eyes conditions, elect to conduct one or more of:
- maintaining a record of those assessments, such as locally at the digital eyewear 100 or at a logically remote database; or
- otherwise maintaining records as necessary or desirable.

At a step 683, the eyewear controller 160 can, responsive to the presence/likelihood or severity of current or future dry eyes conditions, elect to conduct one or more of:
- informing the patient 180 of those assessments;
- informing other digital eyewear 100 or other devices of those assessments;
- informing emergency responders or medical personnel;
- informing the medical personnel 640 who conducted the original assessment, of conditions relating to real-time assessment;
- informing other medical personnel with respect to treatment of the patient's (180) eyes; or otherwise informing devices or personnel as necessary or desirable.

As part of this step, the eyewear controller 160 can inform the medical personnel 640 who conducted the original assessment of information relating to progression of the patient's (180) eye conditions, such as dry eyes conditions, staining or damage to the patient's (180) eye, other conditions related to the patient's (180) eye conditions or eye health, or other information of interest or value to medical personnel 640. This can have the effect that the patient 180 need not appear at the medical personnel's (640) office for as many visits, such as visits disposed to determine the patient's (180) eye conditions or eye health.

At a step 684, the eyewear controller 160 can, responsive to the presence/likelihood or severity of current or future dry eyes conditions, elect to conduct one or more of:
- prompting the patient 180 to perform self-care;
- conducting prevention activity using the treatment devices 150;
- conducting treatment activity using the treatment devices 150; or
- otherwise prompting or conducting prevention/treatment activity.

The method 650 proceeds with the next flow point.

Reporting Information about Dry Eyes Conditions

A flow point 690 indicates that the method 650 is ready to report information in response to its real-time determination of dry eyes conditions.

The method 650 can report information about dry eyes conditions, and lack of dry eyes conditions, in association with its real-time assessments. This can have the effect that the real-time assessments can later be used to identify facts most closely correlated with dry eyes conditions. For example, it might be advisable to report those associations to medical personnel 640 to assist with treatment of the patient 180. This can occur in one or more of the following circumstances:

- if the patient 180 is allergic to certain irritants, such as known pollens, salt air, toxins, cigarettes, colognes and perfumes, or other known irritants;
- if the patient 180 is unduly sensitive to pollutants, such as airborne particulates, NOx, smoke, sulfur compounds, or unburned hydrocarbons;
- if the patient 180 is sometimes engaged in low blink-rate activities, such as intensive computer work or video gaming; or
- if the patient 180 otherwise finds themselves in circumstances that have more than a usual amount of association with dry eyes conditions.

The method 650 can also report information about dry eyes conditions, and lack of dry eyes conditions, in association with patient 180 self-reports of dry eyes conditions. This can have the effect that the patient 180 self-reports can later be used to identify facts most closely correlated with dry eyes conditions.

At a step 691, the digital eyewear 100 can receive information with respect to the patient's (180) circumstances, such as whether the patient 180 is subject to particular circumstances associated with dry eyes conditions. For example, the digital eyewear 100 can receive information from the patient 180. In such cases, the patient 180 can provide information to the digital eyewear 100 using an eye gesture; a hand or body gesture; operation of a smartphone, mobile device, computing device, gaming console, television remote, or other electronic device.

At a step 692, the digital eyewear 100 can receive information from the lenses 120, the patient sensors 130, or the ambient sensors 140.

For example, the information from the lenses 120 can include one or more of:

- a measure of glare, luminosity, or another measure of brightness, such as measures that might cause eyestrain or other conditions associated with dry eyes conditions;
- a measure of luminosity at particular frequencies, such as the blue or ultraviolet ranges of the electromagnetic spectrum;
- an image of an object the patient 180 is looking at, possibly identified using object recognition, such as a television set, a computer screen, a smartphone or other mobile device, or another object associated with dry eyes conditions;
- an image of an outdoor scene the patient 180 is looking at, possibly identified using object recognition, such as beach glare, lake or sea snow glare, excess sunlight, or another outdoor scene associated with dry eyes conditions;
- another object possibly associated with dry eyes conditions or other debilitating eye conditions; or
- another set of information possibly receivable from the lenses 120.

For example, the information from the patient sensors 130 can include one or more of:

- a measure of pupil diameter, such as indicating whether the patient 180 is staring at an object, or otherwise allowing too much light into the eye;
- a measure of blink rate, including whether the patient's (180) eye blinks are complete or only partial blinks;
- a measure of tear break-up time;
- a measure of tear film height;
- a measure of tear viscosity;
- another measure of an eye condition associated with the patient 180 and identifiable by the patient sensors 130; or
- another set of information possibly receivable from the patient sensors 130.

For example, the patient sensors 130 can include a camera with the patient's (180) eye in its field of view, in which the camera can operate at 30, 60, or 120 frames per second, or faster. In such cases, the camera can include a relatively high-speed video camera. Alternatively, in such cases, the camera can include a CCD device coupled to a computing device disposed to access relatively high-speed frame retrieval. At the indicated speeds, the patient sensors 130 can detect blink rate and whether blinks are complete or incomplete.

For example, the information from the ambient sensors 140 can include one or more of:

- a location associated with the digital eyewear 100, such as associated with known irritants, including known pollens, pollutants, weather patterns, or other conditions associated with dry eyes conditions;
- a measure of actual weather conditions, such as atmospheric humidity, atmospheric pressure, excessive wind or spray, or other conditions associated with dry eyes conditions;
- a measure of expected weather conditions, such as atmospheric humidity, atmospheric pressure, such as identified in response to a GPS sensor associated with the digital eyewear 100, within information from the GPS sensor can be used to access an external database to obtain a localized weather report;
- another measure of an eye condition associated with the patient 180 and identifiable by the ambient sensors 140; or
- another set of information possibly receivable from the ambient sensors 140.

At a step 693, the digital eyewear 100 can maintain information with respect to the conditions identified in response to the lenses 120, the patient sensors 130, the ambient sensors 140, or otherwise. For example, the electronic control 160 can record that information in memory or mass storage, can send that information to a logically remote database or other device, or can maintain information describing the identified conditions.

At a step 694, the digital eyewear 100 can report information with respect to the conditions identified in response to the lenses 120, the patient sensors 130, the ambient sensors 140, or otherwise, to medical personnel 640 or devices they might use. For example, as part of this step, the digital eyewear 100 can determine whether it is present at the medical personnel's (640) offices, or otherwise is capable of communication with the medical personnel's (640) devices. As part of this step, the digital eyewear 100 can send information to the medical personnel's (640) devices, such as the medical computing device 620.

At a step 694, the medical computing device 620 can update the weights associated with its artificial neural network. As part of this step, the medical computing device 620 can send the updated weights to the digital eyewear 100. This can have the effect that the digital eyewear 100 can maintain a relatively up-to-date set of weights for its artificial neural network, such as up to date to at least the most recent patient 180 visit to the medical personnel's (640) office.

The method 650 proceeds with the next flow point.

End of Method

A flow point 650B indicates that the method 650 is ready to finish. The method 650 finishes operations and cleans up after any ongoing operations. For example, when using an electronic controller, the controlling device de-allocates and possibly erases any terminated storage values. The method 650 performs any terminating routines, and where applicable, transfers power control to a sleep mode or a shutdown mode.

The method 650 can be restarted as triggered by any technique described with respect to the flow point 650A.

Example Sleeping Patient Systems

Figure 7:
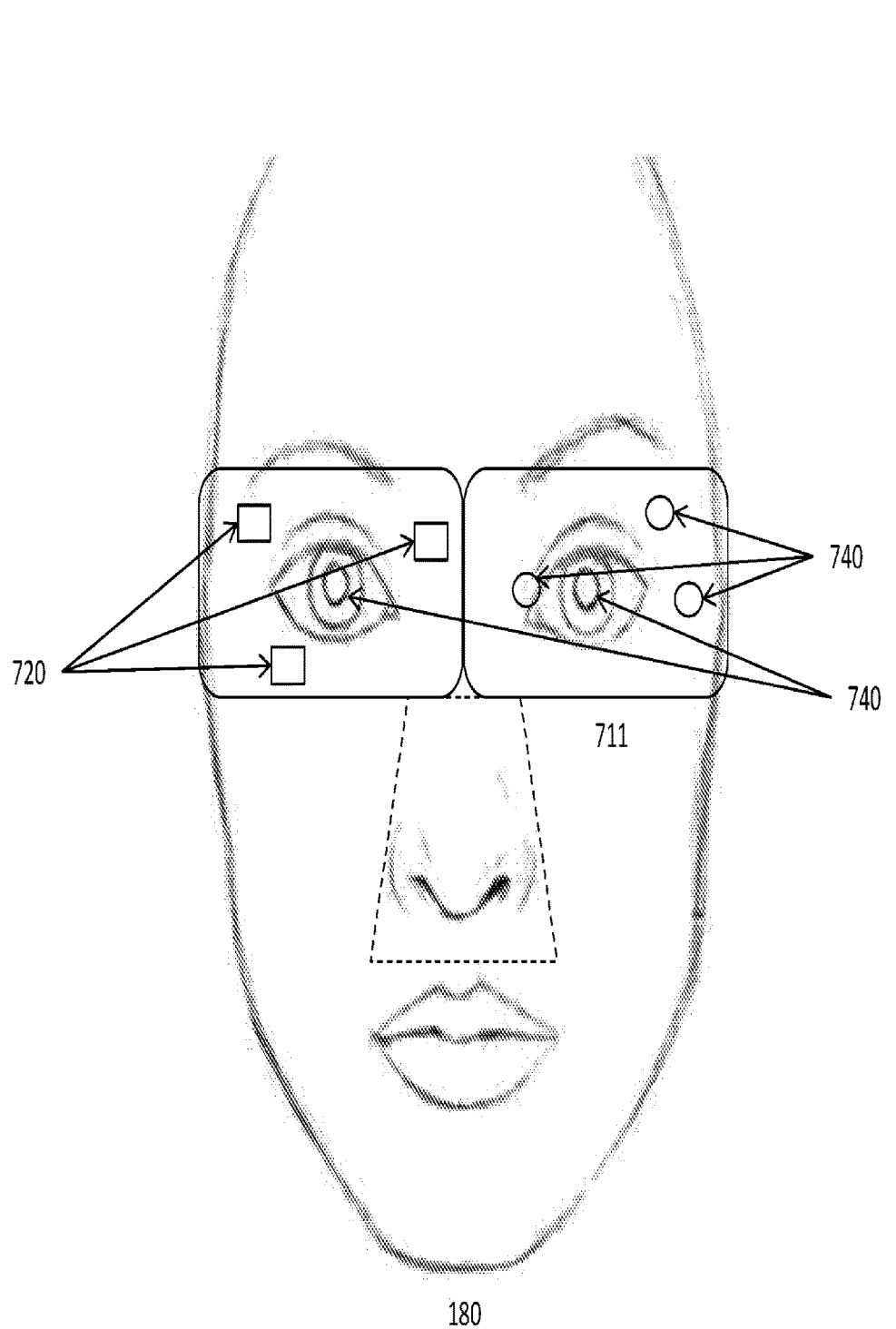
FIG. 7 shows a conceptual drawing of an example system for using digital eyewear with sleeping patients.

FIG. 7 shows a conceptual drawing of an example system for using digital eyewear with sleeping patients.

An example system 700 for using digital eyewear with sleeping patients 180 can include one or more of:
- an eye mask 710;
- an eye movement sensor 720;
- an eye tracking device 730; and
- a sleeping patient dry eyes monitor 740.

In one embodiment, the eye mask 710 can include a relatively opaque cover 711 capable of being disposed over the patient's eyes 180 (shown in the figure as covered by the eye mask 710) such as when the patient 180 is asleep. For example, the eye mask 710 can include a cloth or plastic cover 711 disposed relatively snugly over an area defined by the patient's eyes, and relatively snugly coupled to the patient's face, such as using a rear strap 712 or otherwise. The eye mask 710 can be disposed sufficiently snugly that eye movement, and in particular rapid eye movement (REM) such as exhibited during dream sleep, can be detected from outside the eye mask 711 even when the patient's (180) eyes are closed.

The eye mask 710 can also include a moisture seal 713 and a cushion 714 capable of being disposed to maintain a relatively cool (such as about 1 degree Celsius less than an ambient room temperature) region surrounding the patient's (180) eyes. This can have the effect that the patient's (180) tears are retarded from excessive evaporation, exposure, or other deleterious effects that might occur in response to a warm, dry sleeping area. In such cases, the eye mask 710 can also include a heating element 715 disposed to warm, and possibly compress, the patient's (180) eyes. This can have the effect that operation of the patient's (180) Meibomian glands can be improved, at least temporarily.

The eye mask 710 can also be disposed for coupling to a sleep apnea treatment device 716, such as a CPAP breathing mask or other device coupled to the patient's (180) mouth or nose. This can have the effect that the patient 180 can be treated for sleep apnea concurrently while being treated for one or more dry eyes conditions.

In one embodiment, the eye movement sensor 720 can be disposed to determine when and how the patient's (180) eyes move during eye movement and REM sleep. For example, the eye movement sensor 720 can include a relatively lightweight physical sensor disposed to identify and measure eye movement due to physical changes of the internal pressure on the eye mask 710 from the patient's (180) eyes. For another example, the eye movement sensor 720 can include a device disposed to detect movement of contact lenses, the patient's eye muscles, the patient's pupils, or otherwise, such as by coupling a detector to one or more electromagnetic or ultrasonic effects that can be detected in response to the patient's (180) eye movement.

In one embodiment, the eye tracking device 730 is disposed to receive information from the eye movement sensor 720 and to determine a time-varying measure of eye gaze direction (notwithstanding that the patient's eyes are closed). For example, when the patient 180 moves their eyes during REM sleep, the eye movement sensor 720 can receive information with respect to that movement. In response thereto, the eye tracking device 730 can determine the time-varying directions toward which the patient's eyes are directed. For another example, when the patient 180 opens or closes their eyes during a time when the patient 180 would otherwise be asleep the eye movement sensor 720 can receive information with respect to the patient's (180) eyes being opened or closed. This could occur when the patient 180 blinks at night, during sleep or otherwise; when the patient 180 wakes briefly, even sufficiently briefly that the patient 180 does not recall waking; when the patient 180 brushes their eyes against an obstacle, such as a pillow or sheet; or otherwise.

In one embodiment, the sleeping patient dry eyes monitor 740 can provide information to one or more medical personnel, such as the medical personnel 640 described with respect to FIG. 6A and FIG. 6B.

In one embodiment, the sleeping patient dry eyes monitor 740 can include one or more sensors (not shown) disposed on or near the patient's (180) eyes, such as disposed at an underside of the cover 711 and near the patient's (180) eyelids. For example, the sensors (not shown) can include devices disposed to detect one or more of the following:
- atmospheric dryness near the patient's (180) eyes;
- one or more measures of blood oxygenation, such as a blood oxygenation measure, a breathing rate, or a pulse rate;
- presence of allergies or irritants in or around the patient's (180) eye;
- pressure from inflammation of the patient's (180) eye, or a portion thereof;
- presence of bacteria or bacteriological effects (such as bacteriological effluvia) in or around the patient's (180) eye;
- sleet, tear film debris, or other discharge from patient's (180) eyes;
- symptoms of sleep apnea, such as airway blockage or otherwise;
- any other detectable environmental or systemic effects with respect to the patient's (180) eyes; or
- any other indicators of dry eyes that can be made available even when the patient 180 is sleeping or otherwise has their eyes substantially closed.

In one embodiment, the medical personnel 640 can review information from the system 700. In ordinary circumstances, sleep helps alleviate dry eyes conditions in patients 180 who are sleeping. The medical personnel 640 can, in response to the information from the system 700, assess whether the patient 180 is subject to a dry eyes condition that is not alleviated by sleep.

Alternative Embodiments

Although this Application primarily describes one set of preferred techniques for addressing issues with respect to dry eyes, in the context of the invention, there is no particular requirement for any such limitation. Other techniques for addressing issues with respect to dry eyes would be workable, and could be incorporated with the techniques shown herein.

The invention claimed is:

1. Digital eyewear, including a lens; and
a dynamic eye tracking mechanism coupled to the lens;
wherein the dynamic eye tracking mechanism utilizes optical parameter measurements;
wherein the optical parameter measurements are responsive to one or more of: patient input, patient sensors, ambient sensors, external sensory input, medical personnel;
wherein, responsive to the dynamic eye tracking mechanism and the optical parameter measurements, the eyewear performs procedures for dry eyes effects, the procedures including one or more of: detecting or monitoring, predicting, preventing or treating, training or rewarding patient self-care;
wherein an adjusted sensory input is responsive to the procedures for dry eyes effects;
wherein the optical parameter measurements include at least one measurement of the layers of tears.

2. Digital eyewear as in claim 1,
wherein said adjusted sensory input provides for viewing one or more of:
an advertisement, an external device display, an informational message, a selected person, a selected physical sign, a surface having glare, a n ultraviolet source.

3. Digital eyewear a s in claim 1,
wherein the external device display includes one or more of:
a smartphone, personal computer, laptop, desktop or portable device.

4. Digital eyewear as in claim 1,
wherein said adjusted sensory input is responsive to a polarizing filter.

5. Digital eyewear as in claim 1,
wherein said adjusted sensory input is performed in real time with respect to one or more of:
an external sensory input, a patient dry eyes effect.

6. Digital eyewear as in claim 1,
wherein said adjusted sensory input is utilized with object recognition
to provide an adjusted sensory input;
wherein said adjusted sensory input is less likely than an external sensory input to induce a patient dry eyes effect.

7. Digital eyewear as in claim 1,
wherein a set of parameters is maintained;
wherein said adjusted sensory input is utilized in response to the parameters, the parameters being correlated with one or more of:
a likelihood of the patient currently being subject to a dry eyes effect, or severity thereof;
a likelihood of the patient being subject to a dry eyes effect in a near future;
a likelihood of a treatment being successful at reducing a dry eyes effect in a near future;
a likelihood of a self-care action with respect to a dry eyes effect being conducted by a patient:
a likelihood of a self-care action with respect to a dry eyes effect, if conducted by a patient, being successful;
a likelihood of a patient repeating a particular self-care action with respect to a dry eves effect.

8. Digital eyewear as in claim 7,
wherein the parameters are responsive to one or more of:
a patient input, an ambient sensor, a patient sensor, an external sensory input, a logically remote device, medical personnel, a history of said parameters.

9. Digital eyewear as in claim 1,
wherein said adjusted sensory input is utilized in response to one or more patient conditions and a correlation between those patient conditions and a patient dry eyes effect.

10. Digital eyewear as in claim 9,
wherein the patient conditions are determined in response to one or more of:
ambient sensors, external image input, patient eve activity or other patient sensors, patient input.

11. Digital eyewear, including a lens; and
a dynamic eye tracking mechanism coupled to the lens;
wherein the dynamic eye tracking mechanism utilizes is responsive to one or more of: patient input, patient sensors, ambient sensors, external sensory input, or medical personnel;
wherein, responsive to the dynamic eye tracking mechanism and the optical parameter measurements, the eyewear performs procedures for dry eyes effects, the procedures including one or more of: detecting or monitoring, predicting, preventing or treating, or training or rewarding patient self-care;
wherein an adjusted sensory input is responsive to the procedures for dry eyes effects;
wherein said adjusted sensory input is responsive to translucency shading and reading material.

12. Digital eyewear, including a lens; and
a dynamic eye tracking mechanism coupled to the lens;
wherein the dynamic eye tracking mechanism utilizes optical parameter measurements;
wherein the optical parameter measurements are responsive to one or more of: patient input, patient sensors, ambient sensors, external sensory input, medical personnel;
wherein, responsive to the dynamic eye tracking mechanism and the optical parameter measurements, the eyewear performs procedures for dry eyes effects, the procedures including one or more of: detecting or monitoring, predicting, preventing or treating, training or rewarding patient self-care;
wherein an adjusted sensory input is responsive to the procedures for dry eyes effects;
wherein said adjusted sensory input is utilized in response to one or more patient conditions and a correlation between those patient conditions and a patient dry eyes effect;
wherein the correlation is determined in response to one or more of:
a set of evaluation parameters, a set of information indicating medical correlations with respect to patient dry eyes effects.

13. Digital eyewear as in claim 12,
wherein the medical correlations include historic correlations between two or more of:
a patient condition, an ambient condition, a likelihood of patient dry eyes effects, a measure of patient dry eyes effects, or a measure of whether patient self-care has occurred.

14. A method of operating digital eyewear, including steps of
coupling a dynamic eye tracking mechanism coupled to a lens; utilizing optical parameter measurements to control the dynamic eye tracking mechanism;
wherein the optical parameter measurements are responsive to one or more of: patient input, patient sensors, ambient sensors, external sensory input, or medical personnel;

utilizing shading or inverse-shading in response to the optical parameter measurements;

wherein said shading or inverse-shading is utilized to perform, with respect to dry eyes effects, one or more of:

steps of detecting or monitoring, steps of predicting, steps of preventing or treating, or steps of training or rewarding patient self-care.

15. A method as in claim 14, wherein the steps of utilizing shading or inverse-shading are performed in response to viewing one or more of:

an advertisement, an external device display, an informational message, a selected person, a selected physical sign, a surface having glare, or an ultraviolet source.

16. A method as in claim 14, wherein the external device display includes one or more of:

a smartphone, a personal computer, a laptop, a desktop, or a portable device.

17. A method as in claim 14, wherein the steps of utilizing shading or inverse-shading include using a polarizing filter.

18. A method as in claim 14, wherein the steps of shading or inverse-shading include translucency shading, and are performed in response to reading material.

19. A method as in claim 14, wherein the steps of shading or inverse-shading are performed in real time with respect to one or more of:

an external sensory input, or a patient dry eyes effect.

20. A method as in claim 14, wherein the steps of shading or inverse-shading are performed in response to object recognition to provide an adjusted sensory input;

wherein the adjusted sensory input is less likely than an external sensory input to induce a patient dry eyes effect.

* * * * *